(12) United States Patent
Roh et al.

(10) Patent No.: US 10,035,795 B1
(45) Date of Patent: Jul. 31, 2018

(54) PHENOTHIAZINE DERIVATIVES HAVING CAM INHIBITORY ACTIVITY

(71) Applicant: KOREA INSTITUTE OF SCIENCE AND TECHNOLOGY, Seoul (KR)

(72) Inventors: Eun Joo Roh, Seoul (KR); Bo Ra Mi Jeon, Seoul (KR); Chang Joon Lee, Seoul (KR); Jin Pyo Hong, Seoul (KR); Joo Yeon Jeong, Seoul (KR); Sang Soo Kang, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/480,839

(22) Filed: Apr. 6, 2017

(51) Int. Cl.
*C07D 417/06* (2006.01)
*C07D 279/28* (2006.01)

(52) U.S. Cl.
CPC .......... *C07D 417/06* (2013.01); *C07D 279/28* (2013.01)

(58) Field of Classification Search
CPC .................................................. C07D 417/06
USPC ........................................................... 544/44
See application file for complete search history.

(56) References Cited

U.S. PATENT DOCUMENTS 3,313,810 A * 4/1967 Nakanishi ............ C07D 417/06
544/42

FOREIGN PATENT DOCUMENTS

| DE | 117584 | * | 11/1961 |
| GB | 904209 | * | 3/1960 |
| JP | 41019806 | * | 11/1966 |
| KR | 1979-0001482 B1 | | 10/1976 |
| KR | 1984-0006996 A | | 12/1984 |
| KR | 012275 B1 | | 1/1991 |
| WO | WO 2009/017836 A1 | | 2/2009 |
| WO | WO 2013/060305 A1 | | 5/2013 |

* cited by examiner

*Primary Examiner* — Kahsay Habte
(74) *Attorney, Agent, or Firm* — NSIP Law

(57) ABSTRACT

The present invention provides a phenothiazine derivative or a pharmaceutically acceptable salt thereof, a method of preparing a compound selected therefrom and a pharmaceutical composition containing the compound as an active ingredient. The phenothiazine derivative according to the present invention has an effect of inhibiting calmodulin (CaM; calcium-modulated protein) and thus helps cell death by maintaining the intracellular level of calcium in lung cancer cells at high concentration. Accordingly, the phenothiazine derivative according to the present invention can be usefully used to prevent or treat malignant tumors such as lung cancer.

6 Claims, 2 Drawing Sheets

PHENOTHIAZINE DERIVATIVES HAVING CAM INHIBITORY ACTIVITY

BACKGROUND

(a) Technical Field

The present invention relates to a phenothiazine derivative having CaM inhibitory activity, a method of preparing a compound selected therefrom, and a pharmaceutical composition containing the compound as an active ingredient for preventing and treating lung cancer.

(b) Background Art

At present, the prevalence of cancer in Korea is increasing as the country is becoming an aging society. According to the data published by the Korea Central Cancer Registry in 2013, there were total 218,017 cases of cancer in 2011 in Korea, and among them the cases of lung cancer reached 21,753 and accounted for 1.0% of the total cases. Lung cancer is the leading cancer killer. Lung cancer is a disease characterized by uncontrolled cell growth in tissues of the lung. It may occur as primary tumors or metastatic tumors and is large classified into small-cell lung carcinoma and non-small-cell lung carcinoma depending on size and shape. And, the non-small-cell lung carcinoma is classified into three subtypes, which are squamous cell carcinoma, adenocarcinoma and large-cell carcinoma. Lung cancer is a malignant tumor with low survival rate because its symptoms are not easily detected at early stages.

Lung cancer is treated with various methods including surgery, radiotherapy, chemotherapy, etc. depending on stages. Because non-small-cell lung carcinoma proceeds relatively slowly, complete cure can be expected if detected early. However, because the symptoms are not detected easily in early stages, it is mostly treated by radiotherapy and chemotherapy. For small-cell lung carcinoma, radiotherapy and chemotherapy are essential because it proceeds very quickly and spreads throughout the body as compared to non-small-cell lung carcinoma. However, chemotherapy leads to a range of side effects because it damages not only cancer cells but normal cells that divide rapidly.

Therefore, targeted therapies for inhibiting particular biological mechanisms are being researched and developed. Although gefitinib is currently available for targeted therapy, the drugs that inhibit particular mechanisms can lead to resistance upon long-term medication and may exhibit efficacy under specific conditions only. Thus, a new therapeutic agent for lung cancer is keenly needed. Because the existing targeted therapies are effective in extending survival period but do not provide sufficient therapeutic effect due to toxicity and late detection, development of new therapeutic agents which are effective in those who show resistance to such drugs as gefitinib is necessary.

Calmodulin (CaM; calcium-modulated protein) is a calcium-binding messenger protein expressed in all eukaryotic cells. Once bound to calcium ion, calmodulin acts as part of a calcium signaling transduction pathway by modifying its interactions with various target proteins. It also plays important roles in many physiological processes by regulating a large number of enzymes in the cell. It regulates enzymatic activities as its molecular structure is changed when two calcium ions ($Ca^{2+}$) are bound to CaM.

$IP_3$ receptor is an intracellular calcium ion ($Ca^{2+}$) channel activated by inositol 1,4,5-trisphosphate ($IP_3$) as a second messenger. The $IP_3$ receptor is present in intracellular $Ca^{2+}$ store sites such as the endoplasmic reticulum. When $IP_3$ is bound to the $IP_3$ receptor, the channel pore is opened and $Ca^{2+}$ is released to the cytoplasm ($IP_3$-induced $Ca^{2+}$ release; IICR). IICR is induced as $IP_3$ produced by external stimulation is bound to the $IP_3$ receptor. As a result, the intracellular $Ca^{2+}$ level is increased. The amount of $Ca^{2+}$ released by the $IP_3$ receptor is regulated by CaM. Because high $Ca^{2+}$ concentration in the cell induces cell death, the amount of $Ca^{2+}$ released by the $IP_3$ receptor may be increased by inhibiting the activity of CaM.

TFP is a phenothiazine-based compound mainly used as an antipsychotic [see patent document 1]. Antipsychotics are psychiatric drugs primarily used to manage psychosis such as schizophrenia, bipolar disorder, etc. and also to manage non-psychiatric disorder such as sleep. The antipsychotics tend to block receptors in the brain's dopamine pathways but cover a wide range of drug targets. According to a preceding research, some of the antipsychotics exhibit the effect of inhibiting the growth and differentiation of cancer cells. Based on this, cell viability assay, matrigel invasion assay, colony formation assay and soft agar colony formation assay were conducted to investigate whether TFP suppresses lung cancer. As a result, it was found out that TFP suppresses the migration and proliferation of lung cancer and inhibits the invasion of cancer cells. However, although TFP showed possibility as a drug for lung cancer, experiments revealed that development of candidate materials that can be used at lower concentrations than TFP is necessary.

Although compounds having the phenothiazine backbone are disclosed in several patent documents, they are different in chemical structure from the compounds of the present invention due to the difference in the functional groups attached to the backbone and possibility as an anti-lung cancer drug is not described at all [see patent documents 2, 3 and 4].

Therefore, the inventors of the present invention have synthesized novel phenothiazine derivatives which can be used for lung cancer cells at lower concentrations than TFP (trifluoperazine) and are specific for the lung cancer cells and have found out through experiments that the novel compounds exhibit superior calcium imaging efficiency in lung cancer cells and some of them have much better efficacy than TFP (trifluoperazine).

References of the Related Art

Patent Documents (Patent document 1) International Patent Publication No. WO 2009/017836 "Method and compositions for treating schizophrenia using antipsychotic combination therapy".

(Patent document 2) Korean Patent Publication No. 1979-0001482 "Method for preparing phenothiazine derivatives"

(Patent document 3) Korean Patent Publication No. 1984-0006996 "Method for preparing phenothiazine derivatives"

(Patent document 4) Korean Patent Registration No. 10-0125575 "Phenothiazine derivatives and method for preparing the same"cl SUMMARY The present invention is directed to providing a phenothiazine derivative of a novel structure and a pharmaceutically acceptable salt thereof.

The present invention is also directed to providing a method for preparing the novel compound.

The present invention is also directed to providing a pharmaceutical composition for preventing or treating lung cancer, which contains the novel compound as an active ingredient.

In an aspect, the present invention provides a compound selected from a phenothiazine derivative represented by Chemical Formula 1 and pharmaceutically acceptable salt thereof:

[Chemical Formula 1]

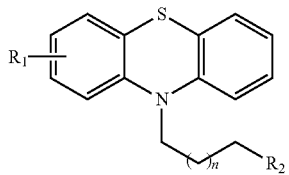

wherein $R_1$ is a hydrogen atom, a halogen atom, a carbonitrile group, a $C_1$-$C_{10}$ alkyl group, a $C_1$-$C_{10}$ haloalkyl group, a $C_1$-$C_{10}$ alkoxy group or a $C_1$-$C_{10}$ alkylthio group;

$R_2$ is

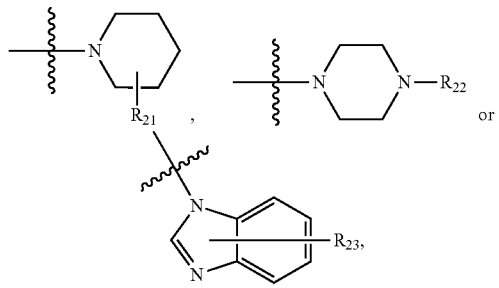

$R_{21}$ is one to three halogen atom(s), a $C_1$-$C_6$ hydroxyalkyl group, a $C_6$-$C_{10}$ aryl group, a $C_6$-$C_{10}$ aryl-$C_1$-$C_6$ alkyl group or a 5- to 7-membered heterocycle group containing one to three hetero atom(s) selected from nitrogen and oxygen atom(s), wherein the aryl or heterocycle group may be substituted or unsubstituted with one to three substituent(s) selected from a group consisting of halo, nitro, $C_1$-$C_6$ alkyl and $C_1$-$C_6$ alkoxy;

$R_{22}$ is one to three halogen atom(s), a $C_6$-$C_{10}$ aryl group, a $C_6$-$C_{10}$ aryl-$C_1$-$C_6$ alkyl group or a 5- to 7-membered heterocycle group containing one to three hetero atom(s) selected from nitrogen and oxygen atom(s), wherein the aryl or heterocycle group may be substituted or unsubstituted with one to three substituent(s) selected from a group consisting of halo, nitro, $C_1$-$C_6$ alkyl and $C_1$-$C_6$ alkoxy;

$R_{23}$ is one to three halogen atom(s), one to three $C_1$-$C_6$ alkyl group(s), a $C_1$-$C_6$ hydroxyalkyl group, a $C_6$-$C_{10}$ aryl group, a $C_6$-$C_{10}$ aryl-$C_1$-$C_6$ alkyl group or a 5- to 7-membered heterocycle group containing one to three hetero atom(s) selected from nitrogen and oxygen atom(s), wherein the aryl or heterocycle group may be substituted or unsubstituted with one to three substituent(s) selected from a group consisting of halo, nitro, $C_1$-$C_6$ alkyl and $C_1$-$C_6$ alkoxy; and n is an integer 1 or 2.

In another aspect, the present invention provides a method for preparing the phenothiazine derivative.

In another aspect, the present invention provides a pharmaceutical composition for preventing and treating lung cancer, which contains a compound selected from the phenothiazine derivative and a pharmaceutically acceptable salt thereof as an active ingredient.

The phenothiazine derivative represented by Chemical Formula 1 according to the present invention has an effect of inhibiting calmodulin (CaM; calcium-modulated protein) and thus helps cell death by maintaining the intracellular level of calcium at high concentration.

Accordingly, the phenothiazine derivative represented by Chemical Formula 1 according to the present invention can be usefully used to prevent or treat malignant tumors such as lung cancer.

DETAILED DESCRIPTION

Figure 1:
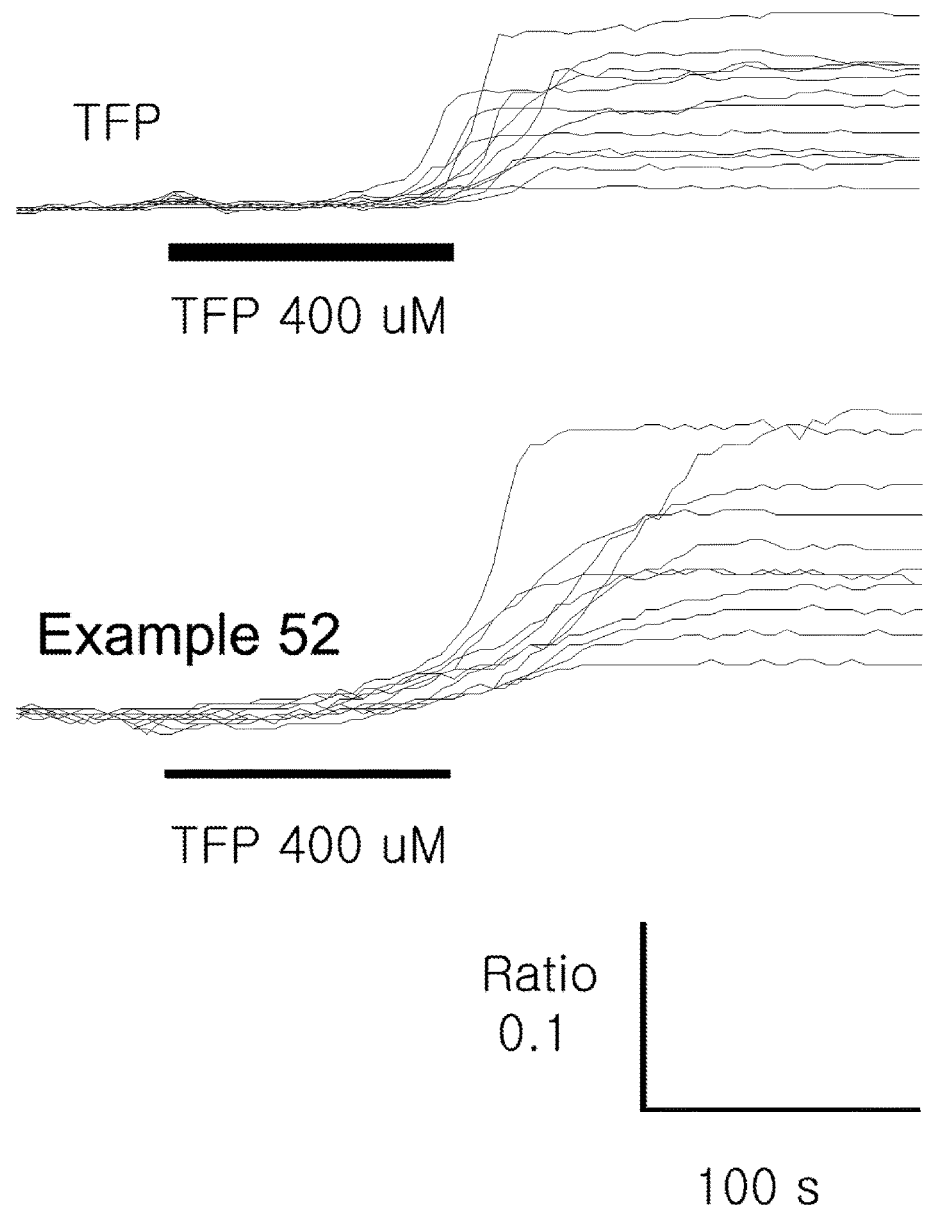
FIG. 1 shows a calcium imaging experiment result for a phenothiazine derivative of the present invention.

The present invention relates to a phenothiazine derivative represented by Chemical Formula 1 or a pharmaceutically acceptable salt thereof:

[Chemical Formula 1]

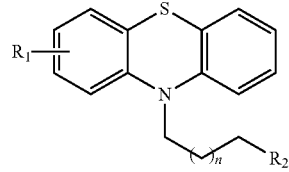

wherein $R_1$ is a hydrogen atom, a halogen atom, a carbonitrile group, a $C_1$-$C_{10}$ alkyl group, a $C_1$-$C_{10}$ haloalkyl group, a $C_1$-$C_{10}$ alkoxy group or a $C_1$-$C_{10}$ alkylthio group;

$R_2$ is

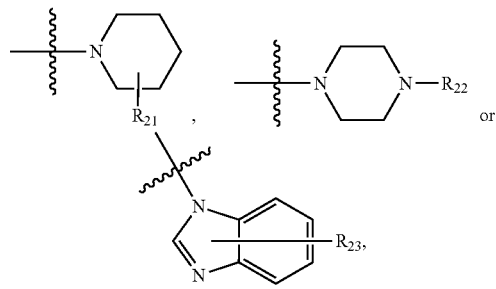

$R_{21}$ is one to three halogen atom(s), a $C_1$-$C_6$ hydroxyalkyl group, a $C_6$-$C_{10}$ aryl group, a $C_6$-$C_{10}$ aryl-$C_1$-$C_6$ alkyl group or a 5- to 7-membered heterocycle group containing one to three hetero atom(s) selected from nitrogen and oxygen atom(s), wherein the aryl or heterocycle group may be substituted or unsubstituted with one to three substituent(s) selected from a group consisting of halo, nitro, $C_1$-$C_6$ alkyl and $C_1$-$C_6$ alkoxy;

$R_{22}$ is one to three halogen atom(s), a $C_6$-$C_{10}$ aryl group, a $C_6$-$C_{10}$ aryl-$C_1$-$C_6$ alkyl group or a 5- to 7-membered heterocycle group containing one to three hetero atom(s) selected from nitrogen and oxygen atom(s), wherein the aryl or heterocycle group may be substituted or unsubstituted with one to three substituent(s) selected from a group consisting of halo, nitro, $C_1$-$C_6$ alkyl and $C_1$-$C_6$ alkoxy;

$R_{23}$ is one to three halogen atom(s), one to three $C_1$-$C_6$ alkyl group(s), a $C_1$-$C_6$ hydroxyalkyl group, a $C_6$-$C_{10}$ aryl group, a $C_6$-$C_{10}$ aryl-$C_1$-$C_6$ alkyl group or a 5- to 7-membered heterocycle group containing one to three hetero atom(s) selected from nitrogen and oxygen atom(s), wherein the aryl or heterocycle group may be substituted or unsubstituted with one to three substituent(s) selected from a group consisting of halo, nitro, $C_1$-$C_6$ alkyl and $C_1$-$C_6$ alkoxy; and n is an integer 1 or 2.

The substituents used to define the compound represented by Chemical Formula 1 according to the present invention are described in more detail. The 'alkyl group' includes both linear and branched hydrocarbon chains having one to ten carbon atom(s). Preferred alkyl groups are methyl, ethyl, propyl, isopropyl, butyl, isobutyl, tert-butyl, etc. The 'alkoxy group' refers to alkyl group bonded to oxygen, wherein the alkyl group is the same as defined above. The 'haloalkyl group' includes both linear and branched hydrocarbon chains having one to thirteen halogen atom(s) such as fluorine, chlorine, bromine and iodine and one to ten carbon atom(s). Preferred haloalkyl groups are fluoromethyl, trifluoromethyl, 1,2-dichloroethyl, 1,1-dichloroethyl, pentafluoroethyl, etc. The 'aryl group' refers to an aromatic ring group with a single ring having at least six atoms or two rings having at least fifteen atoms, wherein adjacent carbon atoms are stabilized by resonance. The aryl group includes phenyl, naphthyl, etc. and the aryl group may be substituted with one or more substituent(s) selected from halo, nitro, $C_1$-$C_6$ alkyl, $C_1$-$C_6$ alkoxy, etc.

Specifically, in the phenothiazine derivative represented by Chemical Formula 1, $R_1$ is a hydrogen atom, a fluorine atom, a chlorine atom, a carbonitrile group, a methyl group, a trifluoromethyl group, a methoxy group or a methylthio group; the $R_2$ is

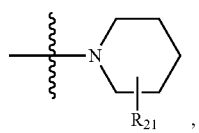

wherein $R_{21}$ is one to three halogen atom(s), a $C_1$-$C_6$ hydroxyalkyl group, a phenyl group, a morpholino group, a pyrrolidinyl group or a piperidinyl group; and the n is an integer 1 or 2.

Also specifically, in the phenothiazine derivative represented by Chemical Formula 1, the $R_1$ is a hydrogen atom, a fluorine atom, a chlorine atom, a carbonitrile group, a methyl group, a trifluoromethyl group, a methoxy group or a methylthio group; the $R_2$ is

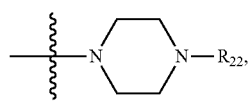

wherein $R_{22}$ is a phenyl group, a benzyl group or a phenethyl group, or a phenyl group, benzyl group or phenethyl group substituted with one to three substituent(s) selected from halo, nitro, $C_1$-$C_6$ alkyl and $C_1$-$C_6$ alkoxy; and the n is an integer 1 or 2.

Also specifically, in the phenothiazine derivative represented by Chemical Formula 1, the $R_1$ is a hydrogen atom, a fluorine atom, a chlorine atom, a carbonitrile group, a methyl group, a trifluoromethyl group, a methoxy group or a methylthio group; the $R_2$ is

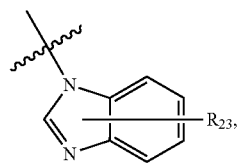

wherein $R_{23}$ is a hydrogen atom or a $C_1$-$C_6$ alkyl group; and the n is an integer 1 or 2.

More specifically, in the phenothiazine derivative represented by Chemical Formula 1, the $R_1$ is a hydrogen atom, a fluorine atom, a chlorine atom, a carbonitrile group, a methyl group, a trifluoromethyl group, a methoxy group or a methylthio group; the $R_2$ is a 4-phenylpiperazin-1-yl group, a 4-(4-nitrophenyl)piperazin-1-yl group, a 4-(2-chlorophenyl)piperazin-1-yl group, a 4-(4-chlorophenyl)piperazin-1-yl group, a 4-(2-fluorophenyl)piperazin-1-yl group, a 4-(4-methoxyphenyl)piperazin-1-yl group, a 4-(3-chlorobenzyl)piperazin-1-yl group, a 4-(4-chlorobenzyl)piperazin-1-yl group, a 4-(4-fluorobenzyl)piperazin-1-yl group, a 4-(p-tolyl)piperazin-1-yl group, a 4-phenethylpiperazin-1-yl group, 4,4-difluoropiperidin-1-yl group, a 4-(hydroxyethyl)piperidin-1-yl group, a 4-phenylpiperidin-1-yl group, a 4-(pyrrolidin-1-yl)piperidin-1-yl group, a 1,4'-bipiperidin-1-yl group, a 4-morpholinopiperidin-1-yl group, a 1H-benzo[d]imidazole group or a 2,5,6-trimethyl-1H-benzo[d]imidazole group; and the n is an integer 1 or 2.

Specific examples of the phenothiazine compound represented by Chemical Formula 1 are as follows:

compound 1.
10-(4-(4-phenylpiperazin-1-yl)butyl)-2-(trifluoromethyl)-10H-phenothiazine;
compound 2.
10-(4-(4-(2-fluorophenyl)piperazin-1-yl)butyl)-2-(trifluoromethyl)-10H-phenothiazine;
compound 3.
10-(3-(4-phenylpiperazin-1-yl)propyl)-2-(trifluoromethyl)-10H-phenothiazine;
compound 4.
10-(3-(4-(4-chlorobenzyl)piperazin-1-yl)propyl)-2-(trifluoromethyl)-10H-phenothiazine;
compound 5.
10-(3-(4-(4-methoxyphenyl)piperazin-1-yl)propyl)-2-(trifluoromethyl)-10H-phenothiazine;
compound 6.
10-(3-(4-(4-nitrophenyl)piperazin-1-yl)propyl)-2-(trifluoromethyl)-10H-phenothiazine
compound 7.
10-(3-(4-(3-chlorobenzyl)piperazin-1-yl)propyl)-2-(trifluoromethyl)-10H-phenothiazine;
compound 8.
10-(3-(4-(4-chlorophenyl)piperazin-1-yl)propyl)-2-(trifluoromethyl)-10H-phenothiazine;
compound 9.
10-(3-(4-(4-fluorobenzyl)piperazin-1-yl)propyl)-2-(trifluoromethyl)-10H-phenothiazine;
compound 10.
10-(3-(4-(2-chlorophenyl)piperazin-1-yl)propyl)-2-(trifluoromethyl)-10H-phenothiazine;

compound 11.
10-(3-(4-p-tolylpiperazin-1-yl)propyl)-2-(trifluoromethyl)-10H-phenothiazine;
compound 12.
10-(3-(4-phenethylpiperazin-1-yl)propyl)-2-(trifluoromethyl)-10H-phenothiazine;
compound 13.
10-(4-(4-(4-nitrophenyl)piperazin-1-yl)butyl)-2-(trifluoromethyl)-10H-phenothiazine;
compound 14.
10-(4-(4-(4-chlorophenyl)piperazin-1-yl)butyl)-2-(trifluoromethyl)-10H-phenothiazine;
compound 15.
2-chloro-10-(4-(4-phenylpiperazin-1-yl)butyl)-10H-phenothiazine;
compound 16.
2-chloro-10-(4-(4-(4-nitrophenyl)piperazin-1-yl)butyl)-10H-phenothiazine;
compound 17.
2-chloro-10-(4-(4-(4-methoxyphenyl)piperazin-1-yl)butyl)-10H-phenothiazine;
compound 18.
2-chloro-10-(4-(4-(4-chlorophenyl)piperazin-1-yl)butyl)-10H-phenothiazine;
compound 19.
10-(4-(4-(4-methoxyphenyl)piperazin-1-yl)butyl)-2-(trifluoromethyl)-10H-phenothiazine;
compound 20.
2-chloro-10-(3-(4-(4-methoxyphenyl)piperazin-1-yl)propyl)-10H-phenothiazine;
compound 21.
2-chloro-10-(3-(4-phenylpiperazin-1-yl)propyl)-10H-phenothiazine;
compound 22.
2-chloro-10-(3-(4-(4-nitrophenyl)piperazin-1-yl)propyl)-10H-phenothiazine;
compound 23.
2-chloro-10-(3-(4-(4-chlorophenyl)piperazin-1-yl)propyl)-10H-phenothiazine;
compound 24.
10-(4-(4-phenylpiperidin-1-yl)butyl)-2-(trifluoromethyl)-10H-phenothiazine;
compound 25.
10-(4-(4-(4-methoxyphenyl)piperazin-1-yl)butyl)-2-(methylthio)-10H-phenothiazine;
compound 26.
2-(methylthio)-10-(4-(4-phenylpiperazin-1-yl)butyl)-10H-phenothiazine;
compound 27.
10-(3-(4-phenylpiperidin-1-yl)propyl)-2-(trifluoromethyl)-10H-phenothiazine;
compound 28.
2-(methylthio)-10-(4-(4-(4-nitrophenyl)piperazin-1-yl)butyl)-10H-phenothiazine;
compound 29.
10-(4-(4-(4-chlorophenyl)piperazin-1-yl)butyl)-2-(methylthio)-10H-phenothiazine;
compound 30.
2-(methylthio)-10-(3-(4-phenylpiperazin-1-yl)propyl)-10H-phenothiazine;
compound 31.
10-(3-(4-(4-chlorophenyl)piperazin-1-yl)propyl)-2-(methylthio)-10H-phenothiazine;
compound 32.
2-(methylthio)-10-(3-(4-(4-nitrophenyl)piperazin-1-yl)propyl)-10H-phenothiazine;
compound 33.
10-(3-(4-(4-methoxyphenyl)piperazin-1-yl)propyl)-2-(methylthio)-10H-phenothiazine;
compound 34.
2-chloro-10-(4-(4-phenylpiperidin-1-yl)butyl)-10H-phenothiazine;
compound 35.
2-chloro-10-(3-(4-phenylpiperidin-1-yl)propyl)-10H-phenothiazine;
compound 36.
2-(methylthio)-10-(3-(4-phenylpiperidin-1-yl)propyl)-10H-phenothiazine;
compound 37.
2-(methylthio)-10-(4-(4-phenylpiperidin-1-yl)butyl)-10H-phenothiazine;
compound 38.
10-(3-(1H-benzo[d]imidazol-1-yl)propyl)-2-(trifluoromethyl)-10H-phenothiazine;
compound 39.
2-(trifluoromethyl)-10-(3-(2,5,6-trimethyl-1H-benzo[d]imidazol-1-yl)propyl)-10H-phenothiazine;
compound 40.
2-(1-(4-(2-(trifluoromethyl)-10H-phenothiazine;-10-yl)butyl)piperidin-4-yl)ethanol;
compound 41.
4-(1-(4-(2-(trifluoromethyl)-10H-phenothiazine;-10-yl)butyl)piperidin-4-yl)morpholine;
compound 42.
10-(4-(4-(pyrrolidin-1-yl)piperidin-1-yl)butyl)-2-(trifluoromethyl)-10H-phenothiazine;
compound 43.
10-(4-(1,4'-bipiperidin-1'-yl)butyl)-2-(trifluoromethyl)-10H-phenothiazine;
compound 44.
4-(1-(4-(2-chloro-10H-phenothiazine;-10-yl)butyl)piperidin-4-yl)morpholine;
compound 45.
4-(1-(4-(2-(methylthio)-10H-phenothiazine;-10-yl)butyl)piperidin-4-yl)morpholine;
compound 46.
4-(1-(3-(2-(trifluoromethyl)-10H-phenothiazine;-10-yl)propyl)piperidin-4-yl)morpholine;
compound 47.
10-(4-(4,4-difluoropiperidin-1-yl)butyl)-2-(trifluoromethyl)-10H-phenothiazine;
compound 48.
10-(3-(4-(pyrrolidin-1-yl)piperidin-1-yl)propyl)-2-(trifluoromethyl)-10H-phenothiazine;
compound 49.
4-(1-(3-(2-chloro-10H-phenothiazine;-10-yl)propyl)piperidin-4-yl)morpholine;
compound 50.
2-chloro-10-(4-(4-(pyrrolidin-1-yl)piperidin-1-yl)butyl)-10H-phenothiazine;
compound 51.
2-chloro-10-(3-(4-(pyrrolidin-1-yl)piperidin-1-yl)propyl)-10H-phenothiazine;
compound 52.
2-(methylthio)-10-(4-(4-(pyrrolidin-1-yl)piperidin-1-yl)butyl)-10H-phenothiazine;
compound 53.
10-(3-(1,4'-bipiperidin-1'-yl)propyl)-2-(trifluoromethyl)-10H-phenothiazine;
compound 54.
4-(1-(3-(2-(methylthio)-10H-phenothiazine;-10-yl)propyl)piperidin-4-yl)morpholine;

compound 55.
2-(methylthio)-10-(3-(4-(pyrrolidin-1-yl)piperidin-1-yl)propyl)-10H-phenothiazine;
compound 56.
10-(4-(4,4-dimethylpiperidin-1-yl)butyl)-2-(trifluoromethyl)-10H-phenothiazine;
compound 57.
4-(1-(4-(10H-phenothiazine;-10-yl)butyl)piperidin-4-yl)morpholine;
compound 58.
10-(4-(4-(pyrrolidin-1-yl)piperidin-1-yl)butyl)-10H-phenothiazine;
compound 59.
10-(4-(1,4'-bipiperidin-1'-yl)butyl)-10H-phenothiazine;
compound 60.
2-methoxy-10-(4-(4-(pyrrolidin-1-yl)piperidin-1-yl)butyl)-10H-phenothiazine;
compound 61.
10-(4-(1,4'-bipiperidin-1'-yl)butyl)-2-methoxy-10H-phenothiazine;
compound 62.
4-(1-(4-(2-methoxy-10H-phenothiazine;-10-yl)butyl)piperidin-4-yl)morpholine;
compound 63.
10-(3-(4-(pyrrolidin-1-yl)piperidin-1-yl)propyl)-10H-phenothiazine;
compound 64.
10-(3-(1,4'-bipiperidin-1'-yl)propyl)-10H-phenothiazine;
compound 65.
4-(1-(3-(10H-phenothiazine;-10-yl)propyl)piperidin-4-yl)morpholine;
compound 66.
10-(3-(1,4'-bipiperidin-1'-yl)propyl)-2-methoxy-10H-phenothiazine;
compound 67.
4-(1-(3-(2-methoxy-10H-phenothiazine;-10-yl)propyl)piperidin-4-yl)morpholine;
compound 68.
2-methoxy-10-(3-(4-(pyrrolidin-1-yl)piperidin-1-yl)propyl)-10H-phenothiazine;
compound 69.
10-(3-(1,4'-bipiperidin-1'-yl)propyl)-2-chloro-10H-phenothiazine;
compound 70.
10-(4-(1,4'-bipiperidin-1'-yl)butyl)-2-chloro-10H-phenothiazine;
compound 71.
10-(3-(1,4'-bipiperidin-1'-yl)propyl)-2-(methylthio)-10H-phenothiazine;
compound 72.
10-(4-(1,4'-bipiperidin-1'-yl)butyl)-2-(methylthio)-10H-phenothiazine;
compound 73.
4-(1-(4-(2-fluoro-10H-phenothiazine;-10-yl)butyl)piperidin-4-yl)morpholine;
compound 74.
2-fluoro-10-(3-(4-methylpiperidin-1-yl)propyl)-10H-phenothiazine;
compound 75.
4-(1-(3-(2-fluoro-10H-phenothiazine;-10-yl)propyl)piperidin-4-yl)morpholine;
compound 76.
2-fluoro-10-(4-(4-methylpiperidin-1-yl)butyl)-10H-phenothiazine;
compound 77.
2-fluoro-10-(4-(4-(pyrrolidin-1-yl)piperidin-1-yl)butyl)-10H-phenothiazine;
compound 78.
10-(4-(1,4'-bipiperidin-1'-yl)butyl)-2-fluoro-10H-phenothiazine;
compound 79.
4-(1-(3-(2-fluoro-10H-phenothiazine;-10-yl)propyl)piperidin-4-yl)morpholine;
compound 80.
10-(3-(1,4'-bipiperidin-1'-yl)propyl)-2-fluoro-10H-phenothiazine;
compound 81.
2-fluoro-10-(3-(4-(pyrrolidin-1-yl)piperidin-1-yl)propyl)-10H-phenothiazine;
compound 82.
3-methyl-10-(4-(4-(pyrrolidin-1-yl)piperidin-1-yl)butyl)-10H-phenothiazine;
compound 83.
10-(4-(1,4'-bipiperidin-1'-yl)butyl)-3-methyl-10H-phenothiazine;
compound 84.
4-(1-(4-(3-methyl-10H-phenothiazine;-10-yl)butyl)piperidin-4-yl)morpholine;
compound 85.
4-(1-(3-(3-methyl-10H-phenothiazine;-10-yl)propyl)piperidin-4-yl)morpholine;
compound 86.
10-(3-(1,4'-bipiperidin-1'-yl)propyl)-3-methyl-10H-phenothiazine;
compound 87.
3-methyl-10-(3-(4-(pyrrolidin-1-yl)piperidin-1-yl)propyl)-10H-phenothiazine;
compound 88.
10-(4-(4-morpholinopiperidin-1-yl)butyl)-10H-phenothiazine-3-carbonitrile;
compound 89.
10-(4-(4-(pyrrolidin-1-yl)piperidin-1-yl)butyl)-10H-phenothiazine-3-carbonitrile;
compound 90.
10-(4-(1,4'-bipiperidin-1'-yl)butyl)-10H-phenothiazine-3-carbonitrile;
compound 91.
2-methyl-10-(4-(4-(pyrrolidin-1-yl)piperidin-1-yl)butyl)-10H-phenothiazine; and
compound 92.
10-(4-(1,4'-bipiperidin-1'-yl)butyl)-2-methyl-10H-phenothiazine.

The phenothiazine compound represented by Chemical Formula 1 according to the present invention may also be used in the form of a pharmaceutically acceptable salt according to methods commonly employed in the art. As the salt, an acid addition salt formed from a pharmaceutically acceptable free acid is useful. The acid addition salt is obtained from an inorganic acid such as hydrochloric acid, nitric acid, phosphoric acid, sulfuric acid, hydrobromic acid, hydroiodic acid, nitrous acid or phosphorous acid or a nontoxic organic acid such as an aliphatic mono- or dicarboxylate, a phenyl-substituted alkanoate, a hydroxyalkanoate, an alkanethioate, an aromatic acid or an aliphatic or aromatic sulfonate. The pharmaceutically acceptable salt includes sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butane-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalane-1-sulfonate, naphthalane-2-sulfonate or mandelate.

The acid addition salt according to the present invention may be prepared by a commonly employed method, for example, by dissolving the compound represented by Chemical Formula 1 in an excess amount of an aqueous acid solution and precipitating a produced salt using a water-miscible organic solvent, e.g., methanol, ethanol, acetone or acetonitrile. Also, it may be prepared by heating equivalent amounts of the compound represented by Chemical Formula 1 and an acid in an aqueous solution or an alcohol and then drying the mixture by evaporation or filtering a precipitated salt by suction.

Also, a pharmaceutically acceptable metal salt may be prepared using a base. The metal salt includes a salt of an alkali metal or an alkaline earth metal and specifically may be prepared as a sodium salt, a potassium salt or a calcium salt. The metal salt is prepared by dissolving the compound represented by Chemical Formula 1 in an excess amount of a solution of an alkali metal hydroxide or an alkaline earth metal hydroxide, removing an undissolved compound by filtration and evaporating and drying the filtrate. Also, a corresponding silver salt may be prepared by reacting the prepared alkali metal salt or alkaline earth metal salt with a suitable silver salt compound (e.g., silver nitrate).

The phenothiazine compound represented by Chemical Formula 1 according to the present invention also includes, in addition to the pharmaceutically acceptable salt, any salt, hydrate or solvate that can be prepared according to commonly employed methods.

The addition salt according to the present invention may be prepared according to a commonly employed method. For example, it may be prepared by dissolving the compound of Chemical Formula 1 in a water-miscible organic solvent, e.g., acetone, methanol, ethanol, acetonitrile, etc., and adding an excess amount of an organic acid or by adding an aqueous solution of an inorganic acid and then performing precipitation or crystallization. Subsequently, the addition salt may be obtained by evaporating the solvent or excess acid from the mixture and then drying the same or by filtering a precipitated salt by suction.

The present invention also provides a method for preparing the phenothiazine compound represented by Chemical Formula 1. As a typical example, the phenothiazine compound represented by Chemical Formula 1 may be prepared by conducting step 1 and step 2 as shown in Scheme 1.

[Scheme 1]

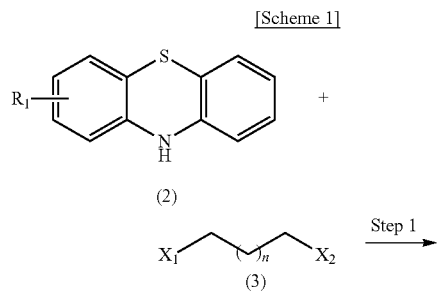

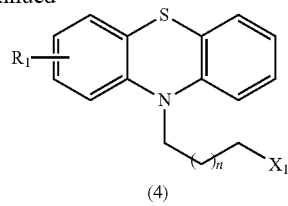

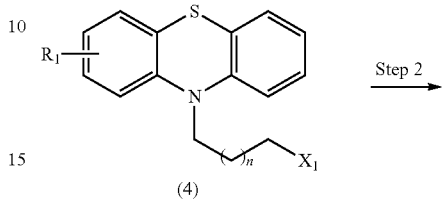

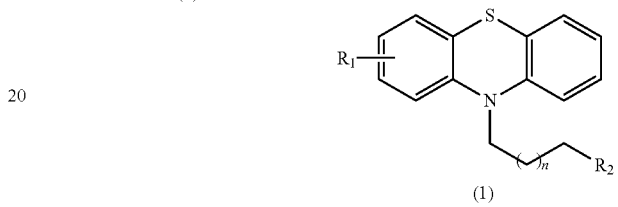

In Scheme 1, each of $R_1$, $R_2$, and n is the same as defined above in Chemical Formula 1 and each of $X_1$ and $X_2$, which are identical or different, is a halogen atom.

The steps of the method for preparing the phenothiazine compound represented by Chemical Formula 1 according to the present invention are described in more detail.

Step 1

In the step 1 of Scheme 1, the haloalkyl-substituted phenothiazine compound represented by Chemical Formula 4 is prepared by reaction of the phenothiazine represented by Chemical Formula 2 as a starting material with the dihaloalkane represented by Chemical Formula 3 compound in a solvent in the presence of a base.

The reaction of the step 1 is widely known in the field of organic chemistry and reaction conditions such as reaction solvent, reaction temperature, reaction time, etc. may be selected adequately in consideration of reactants, products, etc. In the present invention, a hydride, hydroxide, carbonate, hydrogen carbonate or sulfate of an alkali metal, pyridine, etc. may be used as the base. The reaction solvent may be any organic solvent commonly used in the art. Specifically, a halogenated hydrocarbon such as dichloromethane, dichloroethane, etc., an acetate such as ethyl acetate, etc., a nitrile such as acetonitrile, etc., a hydrocarbon such as toluene, etc., an ether such as tetrahydrofuran, diethyl ether, etc., an amide such as N,N-dimethylformamide (DMF), N,N-dimethylacetamide (DMAc), etc., or the like may be used. The reaction temperature may be maintained at 60-150° C., specifically at 90-120° C.

In representative examples of the present invention, the compound represented by Chemical Formula 4 is obtained by heating at 110° C. under reflux using sodium hydride as a base and N,N-dimethylformamide (DMF) as a solvent. However, the present invention is not limited by the examples at all.

Step 2

In the step 2 of Scheme 1, the compound represented by Chemical Formula 1 is prepared by reaction of the compound represented by Chemical Formula 4 with the amine compound represented by $R_2$—H.

The reaction of the step 2 is widely known in the field of organic chemistry and reaction conditions such as reaction solvent, reaction temperature, reaction time, etc. may be selected adequately in consideration of reactants, products, etc. In the present invention, a hydride, hydroxide, carbonate, hydrogen carbonate or sulfate of an alkali metal, pyridine, etc. may be used as the base. The reaction solvent may be any organic solvent commonly used in the art. Specifically, a halogenated hydrocarbon such as dichloromethane, dichloroethane, etc., an acetate such as ethyl acetate, etc., a nitrile such as acetonitrile, etc., a hydrocarbon such as toluene, etc., an ether such as tetrahydrofuran, diethyl ether, etc., an amide such as N,N-dimethylformamide (DMF), N,N-dimethylacetamide (DMAc), etc., a ketone such as acetone, etc., or the like may be used. The reaction temperature may be maintained at 60-150° C., specifically at 90-120° C.

In representative examples of the present invention, the compound represented by Chemical Formula 1 is obtained by heating at 110° C. under reflux using calcium carbonate as a base and a solvent selected from 2-butanone, acetone or ethyl acetate. However, the present invention is not limited by the examples at all.

The compound represented by Chemical Formula 1 prepared through the steps 1 and 2 may be purified by general separation and purification processes, for example, by dilution and washing with an organic solvent, concentration of the organic layer under reduced pressure and, if necessary, column chromatography.

The phenothiazine represented by Chemical Formula 2 which is used as a starting material in Scheme 1 may be either purchased commercially or synthesized according to a method known in the art. When the phenothiazine represented by Chemical Formula 2 is synthesized according to a method known, it may be prepared, for example, by refluxing 2-bromo-1-iodobenzene at 100-150° C. for two days in a dimethyl sulfoxide solvent in the presence of calcium carbonate as a base, copper iodide (CuI) and L-proline.

The present invention also provides a pharmaceutical composition for preventing and treating lung cancer, which contains the phenothiazine derivative represented by Chemical Formula 1 according to the present invention or a pharmaceutically acceptable salt thereof as an active ingredient.

When the composition of the present invention is used as a medicine, the pharmaceutical composition containing the phenothiazine derivative represented by Chemical Formula 1 or a pharmaceutically acceptable salt thereof as an active ingredient may be administered clinically after being prepared into various formulations for oral or parenteral administration described below, although not being limited thereto.

Formulations for oral administration may include, for example, a tablet, a pill, a hard/soft capsule, a liquid, a suspension, an emulsion, a syrup, a granule, an elixir, etc. These formulations contain, in addition to the active ingredient, a diluent (e.g., lactose, dextrose, sucrose, mannitol, sorbitol, cellulose and/or glycine) and a lubricant (e.g., silica, talc, stearic acid and its magnesium or calcium salt and/or polyethylene glycol). The tablet may contain a binder such as magnesium aluminum silicate, starch paste, gelatin, methylcellulose, sodium carboxymethyl cellulose and/or polyvinylpyrrolidone and, optionally, a disintegrant such as starch, agar and alginic acid or its sodium salt, an azeotrope, an absorbent, a colorant, a flavorant and a sweetener.

The pharmaceutical composition containing the derivative rep represented by Chemical Formula 1 as an active ingredient may be administered parenterally. The parenteral administration is performed by subcutaneous injection, intravenous injection, intramuscular injection or intrathoracic injection. For the parenteral administration, the compound represented by Chemical Formula 1 or a pharmaceutically acceptable salt thereof may be prepared into a solution or a suspension by mixing in water with a stabilizer or a buffer and transferring the same to a unit dosage form of an ampoule or a vial. The composition may be sterilized if necessary. It may contain an adjuvant such as an antiseptic, a stabilizer, a wetting agent, an emulsification accelerator, a salt and/or a buffer for control of osmotic pressure, etc. or other therapeutically useful materials and may be formulated according to common mixing, granulation or coating methods.

The administration dosage of the compound represented by Chemical Formula 1 for a human may vary depending on the age, body weight and sex of a patient, administration type, health condition and severity of a disease. For an adult patient weighing 70 kg, a general dosage is 0.01-1,000 mg/day, specifically 1-500 mg/day, and may be administered once or several times a day with predetermined time intervals at the discretion of a physician or a pharmacist.

EXAMPLES

The present invention will be described in more detail through examples and experimental examples. The following examples and experimental examples are for illustrative purposes only and it will be apparent to those skilled in the art that the scope of this invention is not limited by the examples and experimental examples.

Examples

Example 1

Preparation of 10-(4-(4-phenylpiperazin-1-yl)butyl)-2-(trifluoromethyl)-10H-phenothiazine

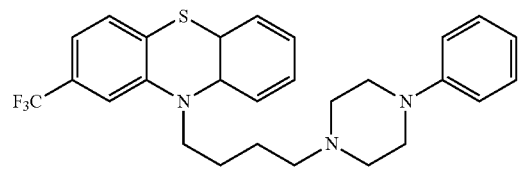 [SMILES: FC(F)(F)c1ccc2c(c1)N(CCCCN1CCN(c3ccccc3)CC1)C1C=CC=CC1S2]

Step 1:
Preparation of 10-(4-chlorobutyl)-2-(trifluoromethyl)-10H-phenothiazine

After dissolving 2-(trifluoromethyl)-10H-phenothiazine (2.0 g, 7.48 mmol) in N,N-dimethylformamide (2 mL), 60% sodium hydride (149.70 mg, 3.74 mmol) and 1-bromo-4-chlorobutane (1.16 mL, 10.10 mmol) were added at 0° C. The reactants were heated at 100° C. for 12 hours under reflux. After the reaction was completed, the reaction solution was extracted with ethyl acetate and the organic layer was dried with magnesium sulfate, filtered under reduced pressure and then concentrated under reduced pressure. The target compound (1.52 g) was obtained with a yield of 56.72% by separating the residue by chromatography (ethyl acetate/n-hexane=1/20).

$^1$H NMR (400 MHz, CDCl$_3$): δ 1.89-2.00 (4H, m, 2CH$_2$), 3.40 (1H, t, J=6.02 Hz, CH), 3.54 (1H, t, 6.18 Hz, CH), 3.94 (2H, t, 6.02 Hz, CH$_2$), 6.89 (1H, d, J=8.12 Hz, CH), 6.96 (1H, t, 7.44 Hz, CH) 7.03 (1H, s, CH), 7.13-7.17 (2H, m, 2CH), 7.21 (2H, t, 8.16 Hz, 2CH).

Step 2:

Preparation of 10-(4-(4-phenylpiperazin-1-yl)butyl)-2-(trifluoromethyl)-10H-phenothiazine After dissolving 10-(4-chlorobutyl)-2-(trifluoromethyl)-10H-phenothiazine (100 mg, 0.279 mmol) in 2-butanone (2 mL) and adding potassium carbonate (77.25 mg, 0.56 mmol), sodium iodide (83.8 mg, 0.56 mmol) and 1-phenylpiperazine (90.68 mg, 0.56) dropwise, the mixture was heated at 80° C. for 24 hours under reflux. After the reaction was completed, the mixture was extracted with ethyl acetate. The organic layer was dried with magnesium sulfate, filtered under reduced pressure and then concentrated under reduced pressure. The target compound (115 mg) was obtained with a yield of 81.48% by separating the residue by chromatography (ethyl acetate/n-hexane=1/2).

$^1$H NMR (400 MHz, CDCl$_3$): δ 1.64-1.70 (2H, m, CH$_2$), 1.82-1.90 (2H, m, CH$_2$), 2.40 (2H, t, J=7.2 Hz, CH$_2$), 2.52-2.54 (4H, m, 2CH$_2$), 3.12-3.15 (4H, m, 2CH$_2$), 3.91 (2H, t, J=6.8 Hz, CH$_2$), 6.84 (1H, dd, J=7.3, 7.2 Hz, CH), 6.89-6.95 (4H, m, 4CH), 7.02 (1H, s, CH), 7.11-7.20 (4H, m, 4CH), 7.22-7.27 (2H, m, 2CH).

The following phenothiazine compounds were synthesized in the same manner as in Example 1. Their structures and $^1$H NMR data are given in Table 1.

TABLE 1

| Ex. | Chemical structure | $^1$H NMR (ppm) δ |
| --- | --- | --- |
| 2 | 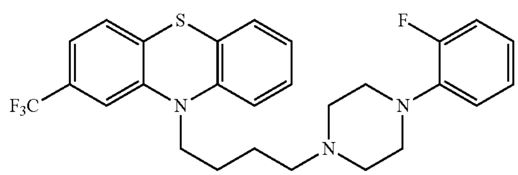 [SMILES: Fc1ccccc1N1CCN(CCCCN2c3ccccc3Sc3ccc(C(F)(F)F)cc32)CC1] | 1.62-1.70 (m, 2H), 1.83-1.89 (m, 2H), 2.42(t, J = 7.2 Hz, 2H), 2.55-2.56 (m, 4H), 3.03-3.0 (m, 4H), 3.92 (t, J = 6.8 Hz, 2H), 6.90-6.98 (m, 4H), 6.98-7.03 (m, 3H), 7.11-7.20 (m, 4H) |
| 3 | 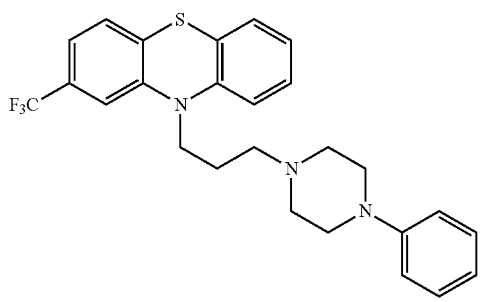 [SMILES: FC(F)(F)c1ccc2c(c1)N(CCCN1CCN(c3ccccc3)CC1)c1ccccc1S2] | 1.94-2.04 (m, 2H), 2.51-2.58 (m, 6H), 3.12-3.15 (m, 4H), 3.98-4.01 (m, 2H), 6.84 (dd, J = 7.3, 7.2 Hz, 1H), 6.89-6.96 (m, 4H), 7.05 (s, 1H), 7.11-7.18 (m, 4H), 7.20-7.27 (m, 2H) |
| 4 | 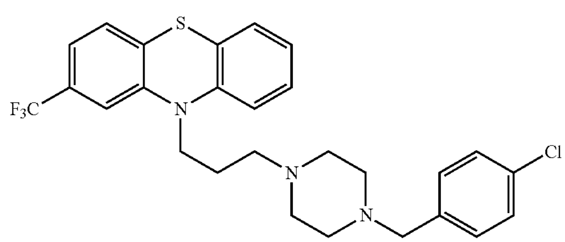 [SMILES: FC(F)(F)c1ccc2c(c1)N(CCCN1CCN(Cc3ccc(Cl)cc3)CC1)c1ccccc1S2] | 1.91-1.96 (m, 2H), 2.40-2.49 (m, 10H), 3.43 (s, 1H), 3.93-3.96 (m, 2H), 6.90-6.95 (m, 2H), 7.03 (s, 1H), 7.09-7.19 (m, 4H), 7.22-7.51 (m, 4H) |
| 5 | 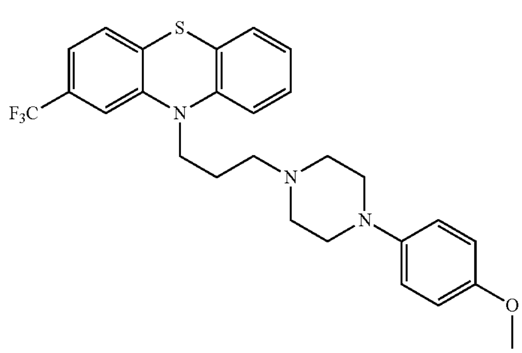 [SMILES: COc1ccc(N2CCN(CCCN3c4ccccc4Sc4ccc(C(F)(F)F)cc43)CC2)cc1] | 1.96-2.01 (m, 2H), 2.52-2.58 (m, 6H), 3.02-3.05 (m, 4H), 3.77 (s, 3H), 3.97-4.01 (t, J = 6.7 Hz, 2H), 7.05 (s, 1H), 7.11-7.18 (m, 4H), 7.20-7.27 (m, 2H) |

TABLE 1-continued

| Ex. | Chemical structure | $^1$H NMR (ppm) δ |
|---|---|---|
| 6 | 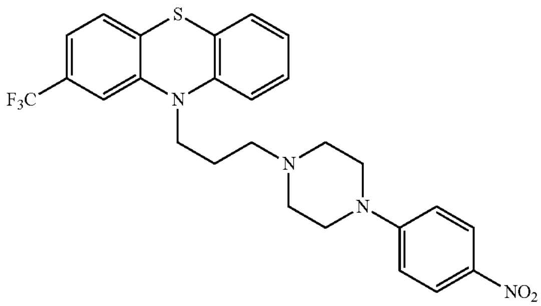 [SMILES: O=[N+]([O-])c1ccc(N2CCN(CCCN3c4ccccc4Sc4ccc(C(F)(F)F)cc43)CC2)cc1] | 1.95-1.99 (m, 2H), 2.52-2.55 (m, 6H), 3.32-3.35 (m, 4H), 4.00-4.03 (m, 2H), 6.78 (d, J = 9.3 Hz, 2H), 6.92-6.98 (m, 2H), 7.06 (s, 1H), 7.12-7.22 (m, 4H), 7.11 (d, J = 9.2 Hz, 2H) |
| 7 | 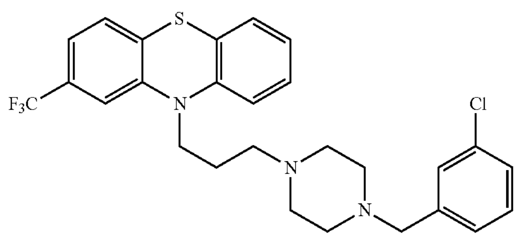 [SMILES: FC(F)(F)c1ccc2c(c1)N(CCCN1CCN(Cc3cccc(Cl)c3)CC1)c1ccccc1S2] | 1.88-1.95 (m, 2H), 2.41-2.48 (m, 10H), 3.43 (s, 2H), 3.94 (d, J = 6.7 Hz, 2H), 6.89-6.95 (m, 2H), 7.03 (s, 1H), 7.08-7.25 (m, 7H), 7.31 (s, 1H) |
| 8 | 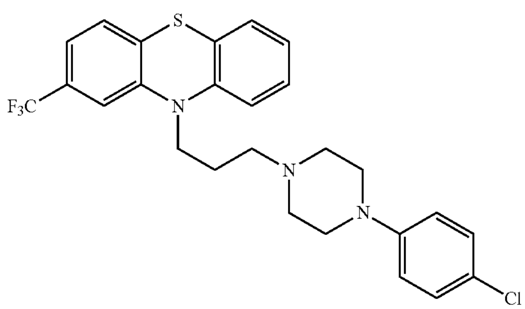 [SMILES: FC(F)(F)c1ccc2c(c1)N(CCCN1CCN(c3ccc(Cl)cc3)CC1)c1ccccc1S2] | 1.95-1.99 (m, 2H), 2.51-2.56 (m, 6H), 3.08-3.10 (m, 4H), 4.00 (t, J = 6.7 Hz, 2H), 6.81 (d, J = 9.0 Hz, 2H), 6.92-6.97 (m, 2H), 7.05 (s, 1H), 7.12-7.21 (m, 6H) |
| 9 | 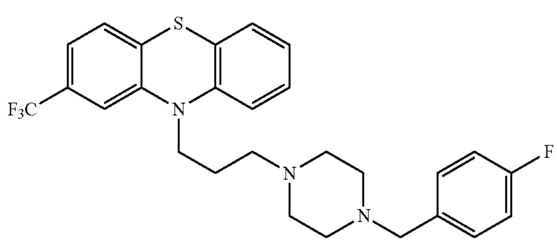 [SMILES: Fc1ccc(CN2CCN(CCCN3c4ccccc4Sc4ccc(C(F)(F)F)cc43)CC2)cc1] | 1.89-1.96 (m, 2H), 2.42-2.49 (m, 10H), 3.43 (s, 2H), 4.00 (t, J = 6.9 Hz, 2H), 6.90-7.00 (m, 4H), 7.03 (s, 1H), 7.09-7.25 (m, 6H) |
| 10 | 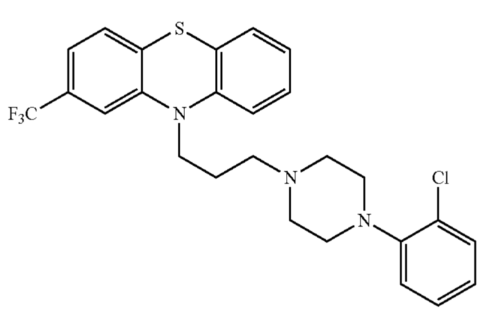 [SMILES: FC(F)(F)c1ccc2c(c1)N(CCCN1CCN(c3ccccc3Cl)CC1)c1ccccc1S2] | 1.94-2.00 (m, 2H), 2.57 (t, J = 6.9 Hz, 2H), 2.60 (s, 4H), 3.01 (s, 4H), 4.00 (t, J = 6.8 Hz, 2H), 6.91-7.00 (m, 3H), 7.02 (d, J = 7.6 Hz, 1H), 7.06 (s, 1H), 7.10-7.24 (m 5H), 7.32-7.34 (m, 1H) |

TABLE 1-continued

| Ex. | Chemical structure | ¹H NMR (ppm) δ |
|---|---|---|
| 11 | 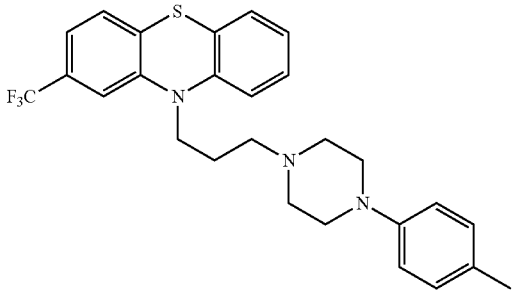 [SMILES: Cc1ccc(N2CCN(CCCN3c4ccccc4Sc4ccc(C(F)(F)F)cc43)CC2)cc1] | 1.96-2.00 (m, 2H), 2.26 (s, 3H), 2.54 (d, J = 6.3 Hz, 2H), 2.58 (t, J = 4.8 Hz, 4H), 3.10 (t, J = 4.78 Hz, 4H), 4.00 (t, J = 6.8 Hz, 2H), 6.83 (d, J = 8.56 Hz, 2H), 6.92-6.96 (m, 2H) 7.07 (d, J = 8.32 Hz, 3H), 7.11-7.21 (m, 4H) |
| 12 | 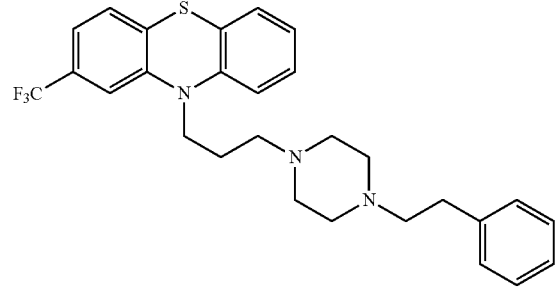 [SMILES: FC(F)(F)c1ccc2c(c1)N(CCCN1CCN(CCc3ccccc3)CC1)c1ccccc1S2] | 1.92-1.99 (m, 2H), 2.49-2.65 (m, 12H), 2.73-2.82 (m, 2H), 4.00 (t, J = 6.8 Hz, 2H), 6.92-6.97 (m, 2H), 7.06 (s, 1H) 7.12-7.22 (m, 7H), 7.27-7.31 (m, 2H) |
| 13 | 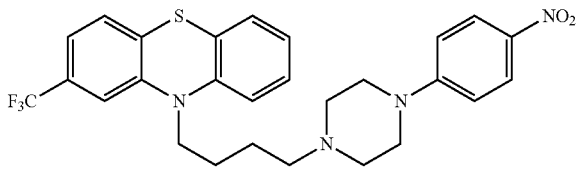 [SMILES: O=[N+]([O-])c1ccc(N2CCN(CCCCN3c4ccccc4Sc4ccc(C(F)(F)F)cc43)CC2)cc1] | 1.63-1.70 (m, 2H), 1.85-1.90 (m, 2H), 2.42 (t, J = 7.0 Hz, 2H), 2.52 (t, J = 5.0 Hz, 4H), 3.35 (t, J = 5.0 Hz, 4H), 4.00 (t, J = 6.7 Hz, 2H), 6.80 (d, J = 9.4 Hz, 2H), 6.90-6.98 (m, 2H) 7.03 (s, 1H), 7.15-7.22 (m, 4H), 8.13 (d, J = 9.4 Hz, 2H) |
| 14 | 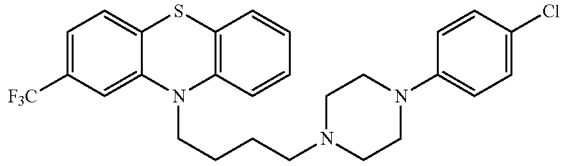 [SMILES: FC(F)(F)c1ccc2c(c1)N(CCCCN1CCN(c3ccc(Cl)cc3)CC1)c1ccccc1S2] | 1.63-1.70 (m, 2H), 1.83-1.91 (m, 2H), 2.42 (t, J = 7.2 Hz, 2H), 2.53 (t, J = 4.9 Hz, 4H), 3.10 (t, J = 4.9 Hz, 4H), 3.95 (t, J = 6.9 Hz, 2H), 6.80-6.82 (m, 2H) 6.22 (d, J = 8.2 Hz, 1H), 6.93-6.97 (m, 1H), 7.03 (s, 1H), 7.12-7.15 (m, 2H), 7.17-7.21 (m, 4H) |
| 15 | 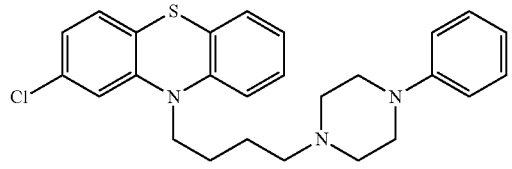 [SMILES: Clc1ccc2c(c1)N(CCCCN1CCN(c3ccccc3)CC1)c1ccccc1S2] | 1.63-1.68 (m, 2H), 1.85-1.91 (m, 2H), 2.43 (t, J = 7.0 Hz, 2H), 2.55 (s, 4H), 3.16 (s, 4H), 3.89 (t, J = 6.9 Hz, 2H), 6.85-6.95 (m, 8H), 7.03 (d, J = 8.1 Hz, 2H), 7.11-7.17 (m, 2H) |
| 16 | 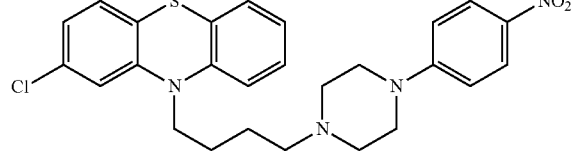 | 1.64-1.68 (m, 2H), 1.86-1.90 (m, 2H), 2.43 (t, J = 7.1 Hz, 2H), 2.53 (t, J = 5.1 Hz, 4H), 3.37 (t, J = 5.1 Hz, 4H), 3.91 (t, J = 6.8 Hz, 2H), 6.78-6.80 (m, 2H), 6.84-6.90 (m, 3H), 6.92-6.96 (m, 1H), 7.04 (d, J = 8.2 Hz, 1H), 7.12-7.17 (m, 2H), 8.10-8.13 (m, 2H) |
| 17 | 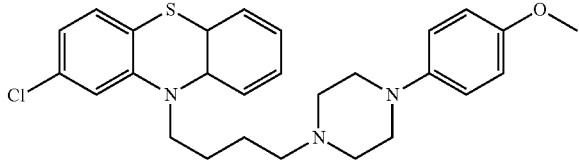 [SMILES: COc1ccc(N2CCN(CCCCN3c4cc(Cl)ccc4SC4C=CC=CC43)CC2)cc1] | 1.65-1.69 (m, 2H), 1.86-1.89 (m, 2H), 2.44 (t, J = 7.2 Hz, 2H), 2.58 (t, J = 4.7 Hz, 4H), 3.08 (t, J = 4.8 Hz, 4H), 3.77 (s, 3H), 3.90 (t, J = 7.0 Hz, 2H), 6.83-6.95 (m, 8H), 7.04 (d, J = 8.2 Hz, 1H), 7.12-7.16 (m, 2H) |

TABLE 1-continued
| Ex. | Chemical structure | ¹H NMR (ppm) δ |
|---|---|---|
| 18 | 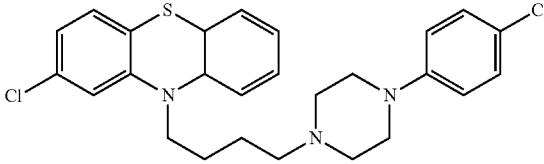 | 1.66-1.67 (m, 2H), 1.85-1.89 (m, 2H), 2.42 (t, J = 7.2 Hz, 2H), 2.54 (t, J = 4.9 Hz, 4H), 3.12 (t, J = 4.9 Hz, 4H), 3.90 (t, J = 6.9 Hz, 2H), 6.81-6.83 (m, 2H), 6.85 (d, J = 2.0 Hz, 1H), 6.87-6.89 (m, 2H), 6.93-6.95 (m, 1H), 7.03 (d, J = 8.1 Hz, 1H), 7.11-7.13 (m, 1H), 7.15-7.17 (m, 1H), 7.18-7.21 (m, 2H) |
| 19 | 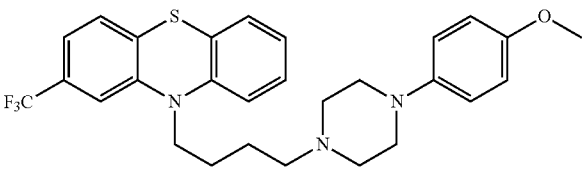 [SMILES: COc1ccc(N2CCN(CCCCN3c4ccccc4Sc4ccc(C(F)(F)F)cc43)CC2)cc1] | 1.65-1.70 (m, 2H), 1.83-1.89 (m, 2H), 2.43 (t, J = 7.3 Hz, 2H), 2.56 (t, J = 4.8 Hz, 4H), 3.05 (t, J = 5.0 Hz, 4H), 3.76 (s, 3H), 3.94 (t, J = 6.9 Hz, 2H), 6.82-6.89 (m, 4H), 6.92 (d, J = 8.7 Hz, 1H), 6.95-6.97 (m, 1H), 7.03 (s, 1H), 7.11-7.13 (m, 1H), 7.15 (s, 1H), 7.21 (t, J = 8.1 Hz, 2H) |
| 20 | 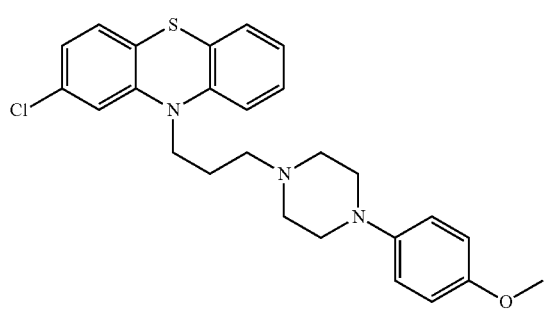 [SMILES: COc1ccc(N2CCN(CCCN3c4ccccc4Sc4ccc(Cl)cc43)CC2)cc1] | 2.01-2.04 (m, 2H), 2.59-2.63 (m, 6H), 3.06-3.10 (m, 4H) 3,76 (s, 3H) 3.96 (t, J = 6.9 Hz, 2H), 6.82-6.92 (m, 7H), 6.95 (d, J = 7.5 Hz, 1H), 7.03 (d, J = 8.0 Hz, 1H), 7.12-7.18 (m, 2H) |
| 21 | 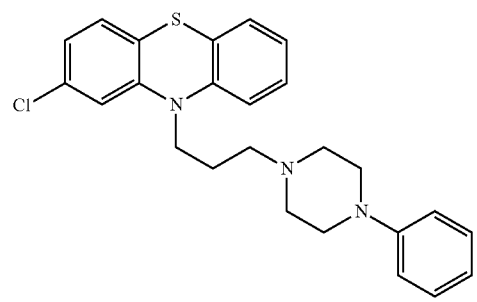 | 1.97-2.00 (m, 2H), 2.51-2.55 (m, 2H), 2.59 (t, J = 4.6 Hz, 4H), 3.18 (t, J = 4.8 Hz, 4H), 3.96 (t, J = 6.9 Hz, 2H), 6.83-6.95 (m, 8H), 7.03 (d, J = 7.9 Hz, 1H), 7.11-7.23 (m, 2H), 7.23 (s, 1H) |
| 22 | 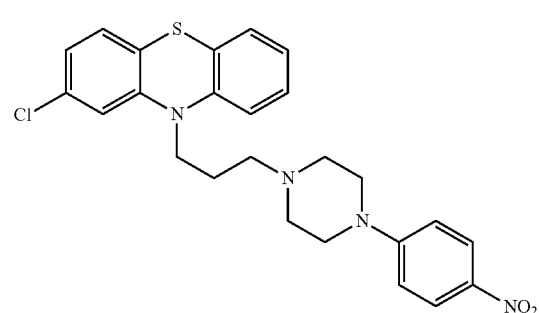 | 1.95-1.98 (m, 2H), 2.51-2.56 (m, 6H), 3.38 (t, J = 5.1 Hz, 4H), 3.98 (t, J = 6.7 Hz, 2H), 6.78-6.81 (m, 2H), 6.87-6.91 (m, 4H) 7.04 (d, J = 8.1 Hz, 1H), 7.11-7.14 (m, 2H), 8.10-8.12 (m, 2H) |
| 23 | 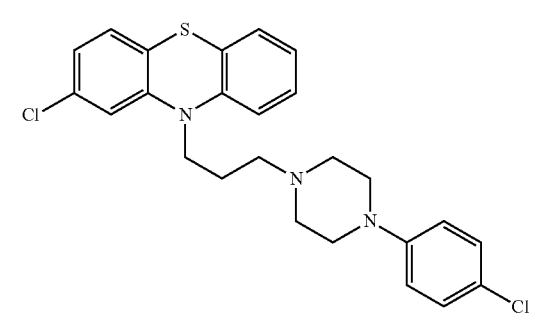 [SMILES: Clc1ccc(N2CCN(CCCN3c4ccccc4Sc4ccc(Cl)cc43)CC2)cc1] | 1.95-2.01 (m, 2H), 2.52 (d, J = 6.8 Hz, 2H), 2.54-2.58 (m, 4H), 3.13 (t, J = 4.7 Hz, 4H), 3.96 (t, J = 6.8 Hz, 2H), 6.80-6.83 (m, 2H), 6.86-6.95 (m, 4H) 7.03 (d, J = 8.0 Hz, 1H), 7.11-7.15 (m, 2H), 7.18-7.20 (m, 2H) |

TABLE 1-continued
| Ex. | Chemical structure | ¹H NMR (ppm) δ |
|---|---|---|
| 24 | 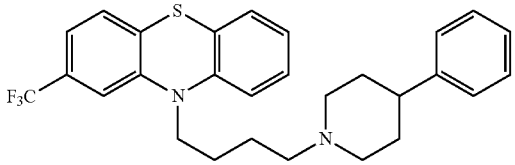 [SMILES: FC(F)(F)c1ccc2c(c1)N(CCCCN1CCC(c3ccccc3)CC1)c1ccccc1S2] | 1.63-1.73 (m, 2H), 1.77-1.80 (m, 4H), 1.83-1.86 (m, 2H), 1.94-1.99 (m, 2H), 2.42 (t, J = 7.1 Hz, 2H), 2.42-2.48 (m, 1H), 2.99 (d, J = 10.8 Hz, 2H), 3.91 (t, J = 6.8 Hz, 2H), 6.89-6.94 (m, 2H), 7.02 (s, 1H), 7.09-7.13 (m, 2H), 7.16-7.22 (m, 5H), 7.26-7.29 (m, 2H) |
| 25 | 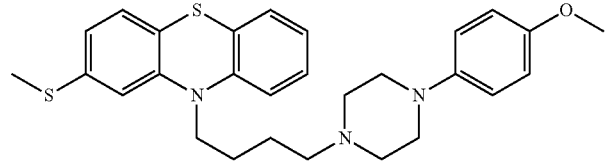 | 1.67-1.69 (m, 2H), 185-1.88 (m, 2H), 2.40-2.42 (m, 2H), 2.46 (s, 3H), 2.52-2.57 (m, 4H), 3.10-3.20 (m, 4H), 3.77 (s, 3H), 3.91 (t, J = 6.0 Hz, 2H), 6.79-6.85 (m, 4H), 6.87-6.93 (m, 4H), 7.10 (d, J = 8.0 Hz, 1H), 7.12-7.18 (m, 2H) |
| 26 | 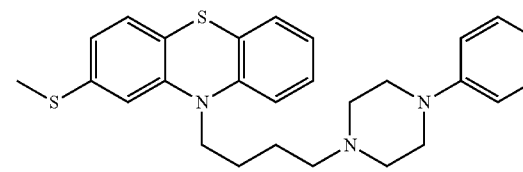 | 1.67-1.69 (m, 2H), 185-1.89 (m, 2H), 2.41-2.42 (m, 2H), 2.45 (s, 3H), 2.53-2.56 (m, 4H), 3.10-3.18 (m, 4H), 3.92 (t, J = 6.9 Hz, 2H), 6.79-6.88 (m, 4H), 6.90-6.93 (m, 4H), 7.06 (d, J = 7.9 Hz, 1H), 7.14 (d, J = 7.5 Hz, 1H), 7.15-7.16 (m, 1H), 7.23-7.25 (m, 1H) |
| 27 | 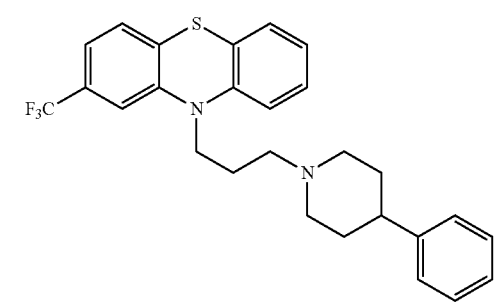 [SMILES: FC(F)(F)c1ccc2c(c1)N(CCCN1CCC(c3ccccc3)CC1)c1ccccc1S2] | 1.72-1.81 (m, 4H), 196-2.06 (m, 4H), 2.41-2.46 (m, 1H), 2.52 (t, J = 7.1 Hz, 2H), 3.00 (d, J = 11.4 Hz, 2H), 4.00 (t, J = 6.7 Hz, 2H), 6.93-6.96 (m, 2H), 7.06 (s, 1H), 7.11-7.13 (m, 1H), 7.15-7.17 (m, 1H), 7.18-7.21 (m, 4H), 7.27-7.31 (m, 3H) |
| 28 | 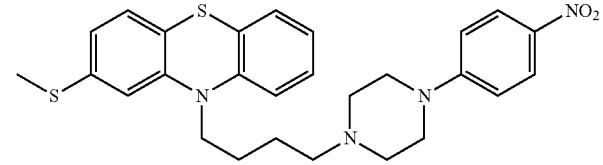 [SMILES: CSc1ccc2c(c1)N(CCCCN1CCN(c3ccc([N+](=O)[O-])cc3)CC1)c1ccccc1S2] | 1.61-1.67 (m, 2H), 1.86-1.89 (m, 2H), 2.42 (t, J = 7.2 Hz, 2H), 2.45 (s, 3H), 2.49-2.51 (m, 4H), 2.35 (t, J = 5.0 Hz, 4H), 3.93 (t, J = 6.8 Hz, 2H), 6.68-6.83 (m, 4H), 6.87-6.92 (m, 2H), 7.10 (d, J = 8.0 Hz, 1H), 7.13-7.15 (m, 2H), 8.10-8.13 (m, 2H) |
| 29 | 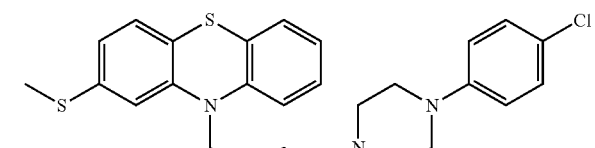 | 1.63-1.68 (m, 2H), 1.83-1.88 (m, 2H), 2.42 (t, J = 6.4 Hz, 2H), 2.45 (s, 3H), 2.49-2.54 (m, 4H), 3.11 (t, J = 5.1 Hz, 4H), 3.92 (t, J = 6.8 Hz, 2H), 6.80-6.83 (m, 4H), 6.87-6.93 (m, 2H), 7.10 (d, J = 8.0 Hz, 1H), 7.12-7.20 (m, 4H) |
| 30 | 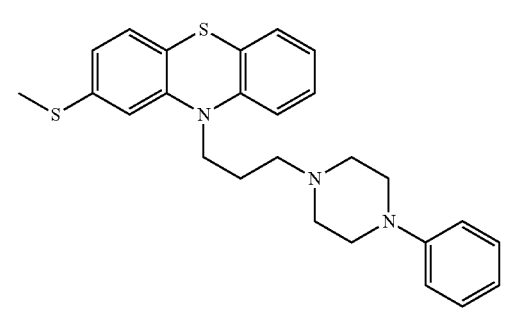 [SMILES: CSc1ccc2c(c1)N(CCCN1CCN(c3ccccc3)CC1)c1ccccc1S2] | 1.97-2.00 (m, 2H), 2.46 (s, 3H), 2.55 (t, J = 8.0 Hz, 2H), 2.56-2.58 (m, 4H), 3.14-3.17 (m, 4H), 3.97 (t, J = 6.8 Hz, 2H), 6.81-6.84 (m, 3H), 6.90-6.93 (m, 4H), 7.03-7.06 (m, 1H), 7.10-7.15 (m, 2H), 7.23-7.25 (m, 2H) |

TABLE 1-continued

| Ex. | Chemical structure | $^1$H NMR (ppm) δ |
|---|---|---|
| 31 | 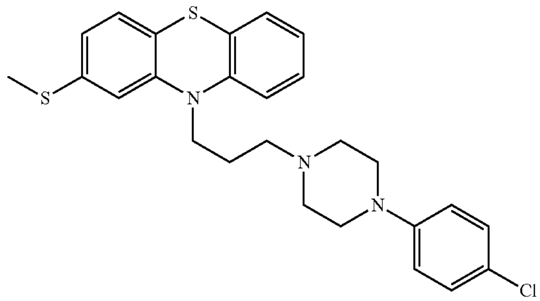 [SMILES: CSc1ccc2c(c1)N(CCCN1CCN(c3ccc(Cl)cc3)CC1)c1ccccc1S2] | 1.96-1.99 (m, 2H), 2.46 (s, 3H), 2.52 (t, J = 8.0 Hz, 2H), 2.54-2.57 (m, 4H), 3.12 (t, J = 6.8 Hz, 4H), 4.00 (t, J = 8.0 Hz, 2H), 6.80-6.83 (m, 4H), 6.89-6.93 (m, 2H), 7.04-7.06 (m, 1H), 7.12-7.14 (m, 2H), 7.17-7.20 (m, 2H) |
| 32 | 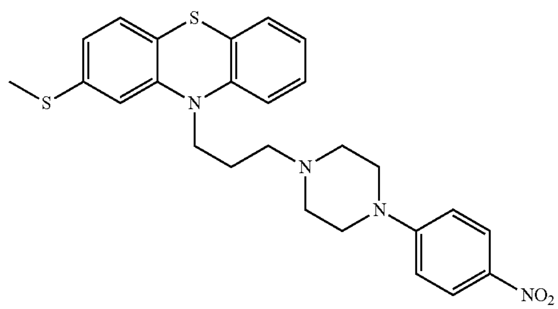 [SMILES: CSc1ccc2c(c1)N(CCCN1CCN(c3ccc([N+](=O)[O-])cc3)CC1)c1ccccc1S2] | 1.95-1.99 (m, 2H), 2.46 (s, 3H), 2.51-2.55 (m, 6H), 3.37 (t, J = 4.9 Hz, 4H), 4.00 (t, J = 6.6 Hz, 2H), 6.78-6.83 (m, 4H), 6.89-6.94 (m, 2H), 7.04-7.06 (m, 1H), 7.13-7.15 (m, 2H), 8.12 (d, J = 9.4 Hz, 2H) |
| 33 | 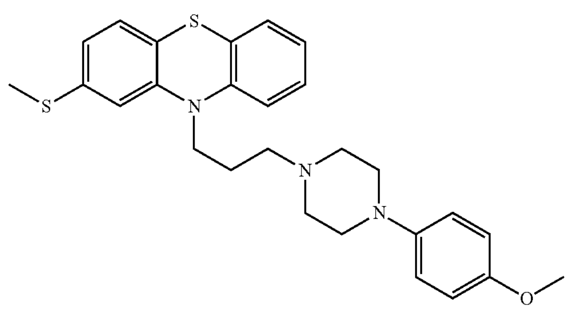 | 1.97-2.00 (m, 2H), 2.46 (s, 3H), 2.55 (t, J = 6.9 Hz, 2H) 2.57-2.59 (m, 4H), 3.06 (m, 4H), 3.76 (s, 3H), 3.97 (t, J = 6.8 Hz, 2H), 6.81-6.84 (m, 4H), 6.86-6.93 (m, 4H), 7.03-7.05 (m, 1H), 7.12-7.14 (m, 2H) |
| 34 | 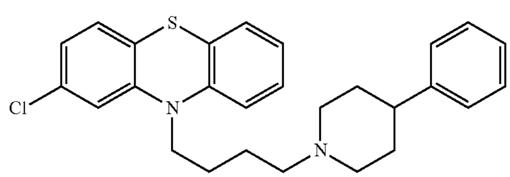 [SMILES: Clc1ccc2c(c1)N(CCCCN1CCC(c3ccccc3)CC1)c1ccccc1S2] | 1.64-1.87 (m, 9H), 1.96-2.02 (m, 2H), 2.41 (t, J = 7.5 Hz, 2H), 3.02 (d, J = 11.4 Hz, 2H), 3.89 (t, J = 7.0 Hz, 2H), 6.84-6.89 (m, 2H), 6.91-6.94 (m, 2H), 7.03 (d, J = 8.1 Hz, 1H), 7.11-7.22 (m, 5H), 7.31 (t, J = 7.6 Hz, 2H) |
| 35 | 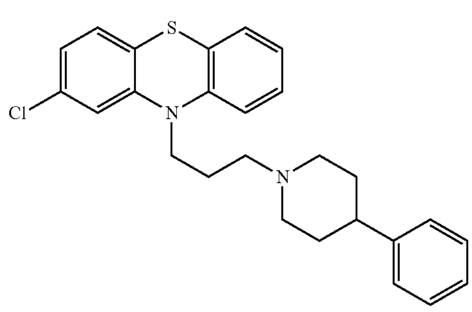 [SMILES: Clc1ccc2c(c1)N(CCCN1CCC(c3ccccc3)CC1)c1ccccc1S2] | 1.70-1.79 (m, 4H), 1.91-2.03 (m, 4H), 2.48 (t, J = 7.4 Hz, 2H), 2.98 (d, J = 11.3 Hz, 2H), 3.90 (t, J = 6.8 Hz, 2H), 6.83-6.92 (m, 4H), 6.95-6.98 (m, 1H), 7.08-7.17 (m, 3H), 7.19-7.20 (m, 2H), 7.25-7.29 (m, 2H) |

TABLE 1-continued

| Ex. | Chemical structure | ¹H NMR (ppm) δ |
| --- | --- | --- |
| 36 | 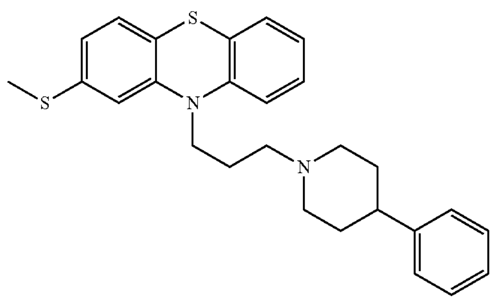 [SMILES: CSc1ccc2c(c1)N(CCCN1CCC(c3ccccc3)CC1)c1ccccc1S2] | 1.26 (s, 1H), 1.72-1.81 (m, 4H), 1.98-2.05 (m, 4H), 2.46 (s, 3H), 2.52 (t, J = 7.3 Hz, 2H), 3.01 (d, J = 11.1 Hz, 2H), 3.95 (t, J = 6.7 Hz, 2H), 6.81-6.82 (m, 2H), 6.89-6.92 (m, 2H), 7.05 (d, J = 8.3 Hz, 1H) 7.11-7.15 (m, 2H), 7.16-7.22 (m, 3H), 7.25-7.30 (m, 2H) |
| 37 | 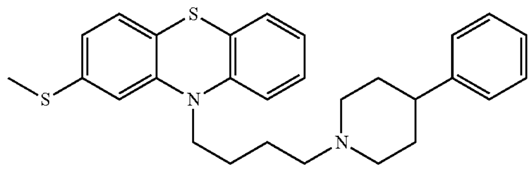 [SMILES: CSc1ccc2c(c1)N(CCCCN1CCC(c3ccccc3)CC1)c1ccccc1S2] | 1.63-1.72 (m, 2H), 1.75-1.78 (m, 4H), 1.80-1.86 (m, 3H), 1.94-2.03 (m, 2H), 2.34 (t, J = 7.4 Hz, 2H), 2.45 (s, 3H), 3.00 (d, J = 11.5 Hz, 2H), 3.90 (t, J = 7.0 Hz, 2H), 6.79 (s, 1H), 6.81 (d, J = 1.8 Hz, 1H), 6.87-6.92 (m, 2H), 7.04 (d, J = 8.0 Hz, 1H), 7.10-7.12 (m, 2H), 7.13-7.14 (m, 1H), 7.15-7.22 (m, 2H), 7.27-7.30 (m, 2H) |
| 38 | 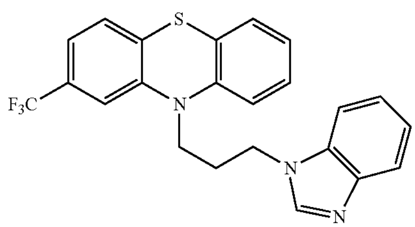 [SMILES: FC(F)(F)c1ccc2c(c1)N(CCCn1cnc3ccccc31)c1ccccc1S2] | 2.29-2.35 (m, 2H), 3.85 (t, J = 5.9 Hz, 2H), 4.29 (t, J = 6.6 Hz, 2H), 6.78 (d, J = 8.0 Hz, 1H), 6.98-7.03 (m, 2H), 7.14-7.18 (m, 3H), 7.19-7.25 (m, 3H), 7.32 (d, J = 8.4 Hz, 1H), 7.65 (s, 1H), 7.76 (d, J = 8.0 Hz, 1H) |
| 39 | 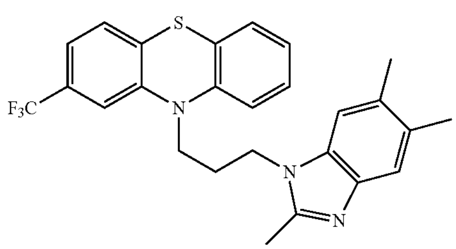 [SMILES: Cc1cc2nc(C)n(CCCN3c4ccccc4Sc4ccc(C(F)(F)F)cc43)c2cc1C] | 2.17 (s, 3H), 2.25-2.29 (m, 2H), 2.30 (s, 3H), 2.35 (s, 3H), 3.97 (t, J = 6.0 Hz, 2H), 4.19 (t, J = 7.2 Hz, 2H), 6.73 (s, 1H), 6.85 (d, J = 8.1 Hz, 1H), 7.02-7.06 (m, 2H), 7.17-7.28 (m, 3H), 7.34 (d, J = 8.0 Hz, 1H), 7.38 (s, 1H) |
| 40 | 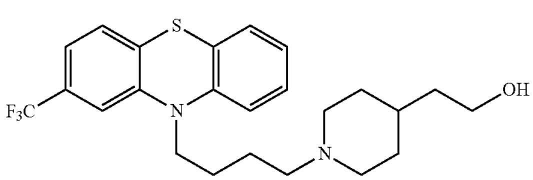 [SMILES: OCCC1CCN(CCCCN2c3ccccc3Sc3ccc(C(F)(F)F)cc32)CC1] | 1.24-1.33 (m, 3H), 1.41-1.51 (m, 3H), 1.60-1.69 (m, 4H), 1.79-1.86 (m, 2H), 1.97 (t, J = 11.0 Hz, 2H), 2.41 (t, J = 7.4 Hz, 2H), 2.94 (d, J = 11.4 Hz, 2H), 3.65 (t, J = 6.4 Hz, 2H), 3.92 (t, J = 6.9 Hz, 2H), 6.89-6.96 (m, 2H), 7.01 (s, 1H), 7.10-7.15 (m, 2H), 7.17-7.20 (m, 2H) |
| 41 | 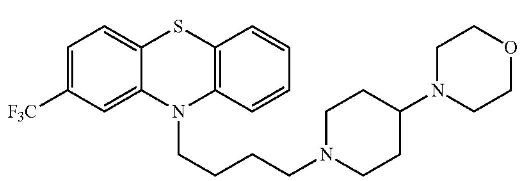 [SMILES: FC(F)(F)c1ccc2c(c1)N(CCCCN1CCC(N3CCOCC3)CC1)c1ccccc1S2] | 1.54-1.56 (m. 2H), 1.64-1.66 (m, 4H), 1.77-1.91 (m, 6H), 2.16-2.19 (m, 1H), 2.52 (t, J = 4.4 Hz, 4H), 2.95 (d, J = 10.2 Hz, 2H), 3.71 (t, J = 4.6 Hz, 4H), 3.91 (t, J = 6.9 Hz, 2H), 6.89 (d, J = 8.1 Hz, 1H), 6.93-6.97 (m, 1H), 7.11-7.21 (m, 4H) |
| 42 | 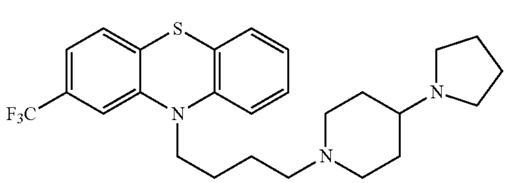 [SMILES: FC(F)(F)c1ccc2c(c1)N(CCCCN1CCC(N3CCCC3)CC1)c1ccccc1S2] | 1.47-1.58 (m, 2H), 1.59-1.65 (m, 2H), 1.77-1.86(m, 8H), 1.89-1.91 (m, 2H), 1.94-1.98 (m, 1H), 2.31 (t, J = 7.2 Hz, 2H), 2.56 (s, 4H), 2.86 (d, J = 11.4 Hz, 2H), 3.89 (t, J = 6.9 Hz, 2H), 6.88-6.95 (m, 2H), 7.01 (s, 1H), 7.10-7.19 (m, 4H) |

TABLE 1-continued

| Ex. | Chemical structure | ¹H NMR (ppm) δ |
|---|---|---|
| 43 | (structure: 2-trifluoromethyl phenothiazine N-(CH₂)₄-piperidine-4-piperidine, 2HCl) | 1.39-1.42 (m, 2H), 1.69-1.75 (m, 4H), 1.77-1.82 (m, 6H), 2.03-2.09 (m, 3H), 2.26-2.33 (m, 2H), 2.87-2.92 (m, 4H), 2.99-3.05 (m, 2H), 3.56 (d, J = 8.3 Hz, 2H), 4.00 (t, J = 6.5 Hz, 2H), 7.03 (t, J = 7.4 Hz, 1H), 7.10 (d, J = 7.9 Hz, 1H), 7.21-7.23 (m, 1H), 7.24-7.27 (m, 2H), 7.29-7.31 (m, 1H), 7.40 (d, J = 8.0 Hz, 1H), 10.14 (s, 1H), 10.44 (s, 1H) |
| 44 | (structure: 2-chloro phenothiazine N-(CH₂)₄-piperidine-4-morpholine) | 1.65-1.66 (m, 2H), 1.73-1.89 (m, 6H), 1.99-2.04 (m, 1H), 2.19-2.21 (m, 2H), 2.34-2.37 (m, 2H), 2.53 (s, 4H), 2.96 (s, 2H), 3.71 (t, J = 4.6 Hz, 4H), 3.86 (t, J = 6.4 Hz, 3H), 6.83 (d, J = 2.0 Hz, 1H), 6.87-6.90(m, 2H), 6.93 (t, J = 7.5 Hz, 1H), 7.03 (d, J = 8.2 Hz, 1H), 7.11-7.17 (m, 2H) |
| 45 | (structure: 2-methylthio phenothiazine N-(CH₂)₄-piperidine-4-morpholine) | 1.76-1.87 (m, 8H), 2.25-2.30 (m, 3H), 2.46 (s, 3H), 2.50 (t, J = 4.3 Hz, 4H), 2.56-2.57 (m, 2H), 3.07 (d, J = 11.2 Hz, 2H), 3.70 (t, J = 4.5 Hz, 4H), 3.89 (t, J = 6.3 Hz, 2H), 6.77 (d, J = 1.6 Hz, 1H), 6.81-6.84 (m, 1H), 6.87 (d, J = 8.0 Hz, 1H), 6.90-6.94 (m, 1H), 7.04 (d, J = 8.0 Hz, 1H), 7.12-7.18 (m, 2H) |
| 46 | (structure: 2-trifluoromethyl phenothiazine N-(CH₂)₃-piperidine-4-morpholine) | 1.35-1.45 (m, 2H), 1.69 (d, J = 12.1 Hz, 2H), 1.83-1.89 (m, 4H), 2.03-2.11 (m, 1H), 2.37 (t, J = 7.0 Hz, 2H), 2.43 (t, J = 4.3 Hz, 4H), 2.83 (d, J = 11.6 Hz, 2H), 3.62 (t, J = 4.5 Hz, 4H), 3.86 (t, J = 6.8 Hz, 2H), 6.81-6.87 (m, 2H), 6.95 (s, 1H), 7.00-7.09 (m, 4H) |
| 47 | (structure: 2-trifluoromethyl phenothiazine N-(CH₂)₄-4,4-difluoropiperidine) | 1.58-1.65 (m, 2H), 1.77-1.95 (m, 6H), 2.38 (t, J = 7.1 Hz, 2H), 2.46 (t, J = 4.9 Hz, 4H), 3.91 (t, J = 6.8 Hz, 2H), 6.89 (d, J = 8.1 Hz, 1H), 6.95 (t, J = 7.5 Hz, 1H), 7.02 (s, 1H), 7.12-7.16 (m, 2H), 7.19 (t, J = 7.8 Hz, 2H) |
| 48 | (structure: 2-trifluoromethyl phenothiazine N-(CH₂)₃-piperidine-4-pyrrolidine) | 1.51-1.61 (m, 2H), 1.82-1.84 (m, 5H), 1.88-1.97 (m, 5H), 2.11-2.18 (m, 1H), 2.43 (t, J = 6.9 Hz, 2H), 2.67 (s, 4H), 2.87 (d, J = 11.8 Hz, 2H), 3.94 (t, J = 6.8 Hz, 2H), 6.93 (t, J = 8.1 Hz, 2H), 7.03 (s, 1H), 7.09-7.19 (m, 4H) |

TABLE 1-continued

| Ex. | Chemical structure | $^1$H NMR (ppm) δ |
|---|---|---|
| 49 | 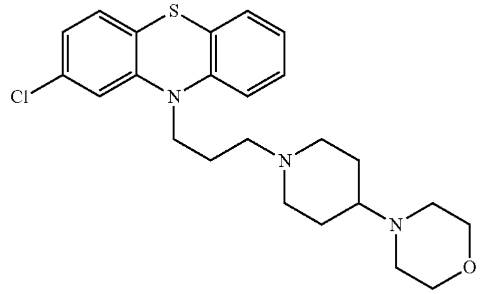 [SMILES: Clc1ccc2c(c1)N(CCCN1CCC(N3CCOCC3)CC1)c1ccccc1S2] | 1.97-1.99 (m, 2H), 2.16-2.20 (m, 2H), 2.87-2.95 (m, 2H), 3.04-3.28 (m, 4H), 3.59 (d, J = 11.2 Hz, 2H), 3.86 (t, J = 12.0 Hz, 2H), 3.95-4.04( m, 4H), 7.00-7.05 (m, 4H), 7.10-7.15 (m, 4H), 7.19-7.27(m, 1H), 10.62 (s, 1H), 11.64 (s, 1H) |
| 50 | 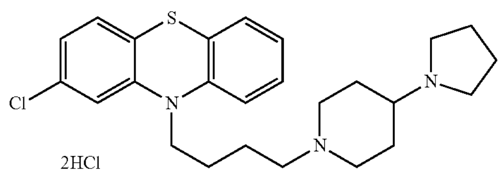 [SMILES: Clc1ccc2c(c1)N(CCCCN1CCC(N3CCCC3)CC1)c1ccccc1S2] | 1.71-1.78 (m, 4H), 1.87-1.90 (m, 2H), 1.97-1.99 (m, 3H), 2.04-2.14 (m, 2H), 2.22-2.25 (m, 2H), 2.82-2.86 (m, 2H), 3.03 (s, 4H), 3.49-3.55 (m, 4H), 4.00 (t, J = 7.8 Hz, 2H), 6.98-7.03 (m, 2H), 7.06-7.10 (m, 2H), 7.17- 7.20 (m, 2H), 7.22-7.26 (m, 1H), 10.17 (s, 1H), 11.22 (s, 1H) |
| 51 | 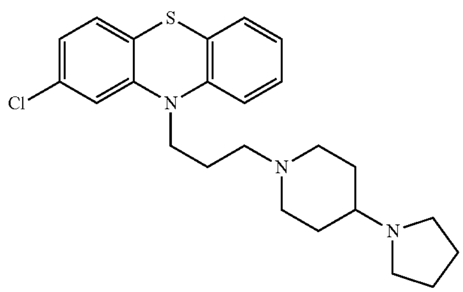 [SMILES: Clc1ccc2c(c1)N(CCCN1CCC(N3CCCC3)CC1)c1ccccc1S2] | 1.25 (t, J = 7.1 Hz, 1H), 1.29-1.58 (m, 2H), 1.79-1.86 (m, 5H), 1.89-1.95 (m, 5H), 2.01-2.06 (m, 1H), 2.40 (t, J = 6.8 Hz, 2H), 2.59 (s, 4H), 2.85 (d, J = 11.4 Hz, 2H), 3.86 (t, J = 6.8 Hz, 2H), 6.82-6.92 (m, 4H), 6.98(d, J = 8.1 Hz, 1H), 7.07-7.15 (m, 2H) |
| 52 | 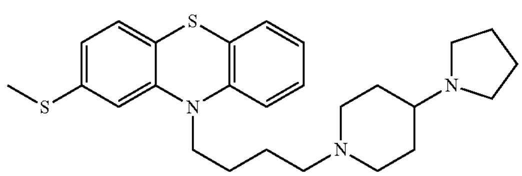 [SMILES: CSc1ccc2c(c1)N(CCCCN1CCC(N3CCCC3)CC1)c1ccccc1S2] | 1.45-1.49 (m, 2H), 1.52-1.61 (m, 2H) 1.76 (s, 4H), 1.78-1.84 (m, 4H), 1.90-1.93 (m, 2H), 1.94-1.97 (m, 1H), 2.29 (t, J = 7.3 Hz, 2H), 2.44 (s, 3H), 2.53 (s, 4H), 2.84 (d, J = 11.3 Hz, 2H), 3.84 (t, J = 6.9 Hz, 2H), 6.76-6.80 (m, 2H), 6.84-6.90 (m, 2H), 7.01 (d, J = 7.9 Hz, 1H), 7.09-7.14 (m, 2H) |
| 53 | 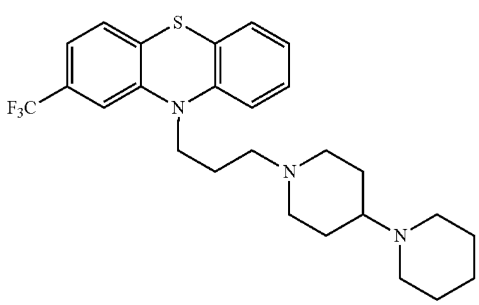 [SMILES: FC(F)(F)c1ccc2c(c1)N(CCCN1CCC(N3CCCCC3)CC1)c1ccccc1S2] | 1.44-1.44 (m, 3H), 1.49-1.53 (m, 2H), 1.61 (s, 4H), 1.75-1.77 (m, 3H), 1.87-1.96 (m, 4H), 2.26-2.28 (m, 1H), 2.43 (t, J = 7.0 Hz, 2H), 2.51 (s, 4H), 2.92 (d, J = 11.5 Hz, 2H), 3.94 (t, J = 6.8 Hz, 2H), 6.91 (d, J = 8.0 Hz, 1H), 6.94-6.96 (m, 1H), 7.03 (s, 1H), 7.10-7.20 (m, 4H) |
| 54 | 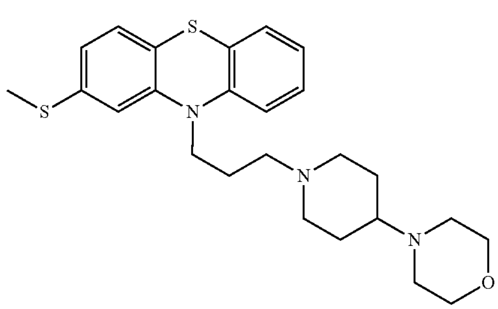 [SMILES: CSc1ccc2c(c1)N(CCCN1CCC(N3CCOCC3)CC1)c1ccccc1S2] | 1.43-1.50 (m, 2H), 1.75-1.79 (m, 2H), 1.87-1.95 (m, 4H), 2.12-2.18 (m, 1H), 2.43 (t, J = 7.3 Hz, 2H), 2.46 (s, 3H), 2.53 (t, J = 4.5 Hz, 4H), 2.92 (d, J = 11.4 Hz, 2H), 3.71 (t, J = 4.6 Hz, 4H), 3.90 (t, J = 6.9 Hz, 2H), 6.80-6.82 (m, 2H), 6.87-6.92 (m, 2H), 7.04 (d, J = 7.8 Hz, 1H), 7.11-7.15 (m, 2H) |

TABLE 1-continued

| Ex. | Chemical structure | ¹H NMR (ppm) δ |
|---|---|---|
| 55 | 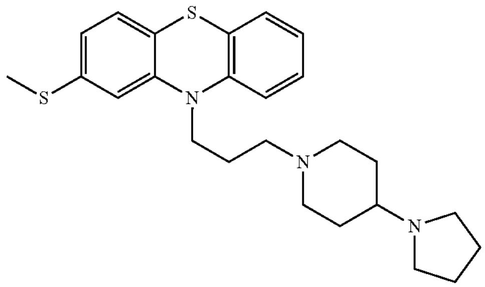 [SMILES: CSc1ccc2c(c1)N(CCCN1CCC(N3CCCC3)CC1)c1ccccc1S2] | 1.50-1.60 (m, 2H), 1.81 (s, 4H), 1.84-1.87 (m, 2H), 1.89-1.96 (m, 4H) 2.04-2.10 (m, 1H), 2.43 (t, J = 7.1 Hz, 2H), 2.46 (s, 3H), 2.61 (s, 4H), 2.87 (d, J = 11.8 Hz, 2H), 3.90 (t, J = 6.9 Hz, 2H), 6.79 (s, 1H), 6.81-6.82 (m, 1H), 6.88-6.92 (m, 2H), 7.03 (d, J = 7.8 Hz, 1H), 7.10-7.16 (m, 2H) |
| 56 | 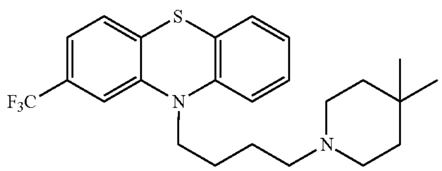 [SMILES: CC1(C)CCN(CCCCN2c3ccccc3Sc3ccc(C(F)(F)F)cc32)CC1] | 0.85 (d, J = 6.8 Hz, 6H), 0.96-1.00 (m, 1H), 1.18-1.28 (m, 2H), 1.37-1.42 (m, 1H), 1.59-1.67 (m, 4H), 1.76-1.86 (m, 4H), 2.31 (t, J = 7.6 Hz, 2H), 2.89 (d, J = 11.4 Hz, 2H), 3.89 (t, J = 7.1 Hz, 2H), 6.90 (d, J = 8.1 Hz, 1H), 6.91-6.95 (m, 1H), 7.01 (s, 1H), 7.10-7.12 (m, 1H), 7.14 (s, 1H), 7.16-7.19 (m, 2H) |
| 57 | 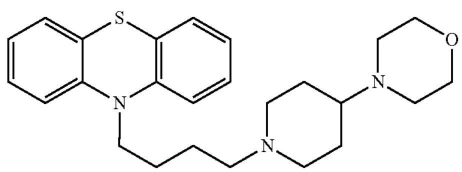 [SMILES: c1ccc2c(c1)Sc1ccccc1N2CCCCN1CCC(N2CCOCC2)CC1] | 1.43-1.53 (m, 2H), 1.57-1.64 (m, 2H), 1.74-1.89 (m, 6H), 2.11-2.19 (m, 1H), 2.31 (t, J = 7.4 Hz, 2H), 2.52 (t, J = 4.6 Hz, 4H), 2.91 (d, J = 11.7 Hz, 2H), 3.70 (t, J = 4.6 Hz, 4H), 3.86 (t, J = 7.0 Hz, 2H), 6.85-6.91 (m, 4H), 7.11-7.15 (m, 4H) |
| 58 | 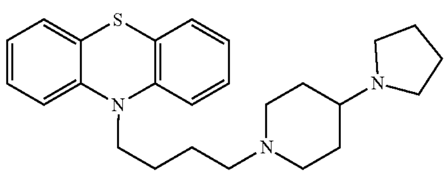 [SMILES: c1ccc2c(c1)Sc1ccccc1N2CCCCN1CCC(N2CCCC2)CC1] | 1.48-1.64 (m, 4H), 1.78-1.92 (m, 10H), 1.97-205 (m, 1H), 2.31 (t, J = 7.3 Hz, 2), 2.58 (s, 4H), 2.86 (d, J = 11.6 Hz, 2H), 3.86 (t, J = 7.0 Hz, 2H), 6.84-6.91 (m, 4H), 7.10-7.15 (m, 4H) |
| 59 | 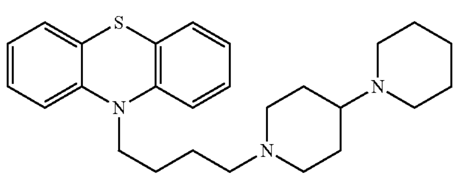 [SMILES: c1ccc2c(c1)Sc1ccccc1N2CCCCN1CCC(N2CCCCC2)CC1] | 1.44-1.46 (m, 2H), 1.51-1.65 (m, 8H), 1.77-1.89 (m, 6H), 2.30-2.35 (m, 3H), 2.55 (s, 1H), 2.94 (d, J = 11.5 Hz, 2H), 3.86 (t, J = 7.0 Hz, 2H), 6.85-6.91 (m, 4H), 7.11-7.15 (m, 4H) |
| 60 | 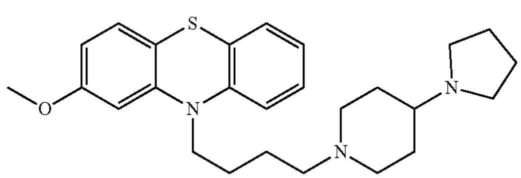 [SMILES: COc1ccc2c(c1)N(CCCCN1CCC(N3CCCC3)CC1)c1ccccc1S2] | 1.50-1.65 (m, 4H), 1.76-1.93 (m, 10H), 2.02-2.09 (m, 1H), 2.32 (t, J = 7.5 Hz, 2H), 2.60 (s, 4H), 2.87 (d, J = 11.8 Hz, 2H), 3.77 (s, 3H), 3.84 (t, J = 7.0 Hz, 2H), 6.46 (s, 1H), 6.48 (d, J = 2.4 Hz, 1H), 6.85-6.91 (m, 2H), 6,99-7.01 (m, 1H), 7.11-7.15 (m, 2H) |
| 61 | 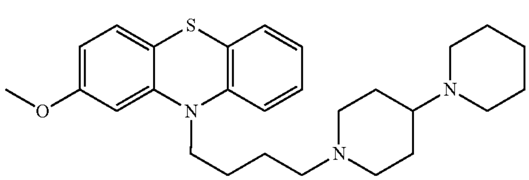 [SMILES: COc1ccc2c(c1)N(CCCCN1CCC(N3CCCCC3)CC1)c1ccccc1S2] | 1.42-1.43 (m, 2H), 1.50-1.64 (m, 8H), 1.71-1.74 (m, 3H), 1.79-1.87 (m, 4H), 2.20-2.26 (m, 1H), 2.31 (t, J = 7.4 Hz, 2H), 2.49 (t, J = 5.0 Hz, 4H), 2.93 (d, J = 11.7 Hz, 2H), 3.77 (s, 3H), 3.84 (t, J = 7.1 Hz, 2H), 6.46-6.49 (m, 2H), 6.86-6.91 (m, 2H), 7.00-7.02 (m, 1H), 7.11-7.14 (m, 2H) |
| 62 | 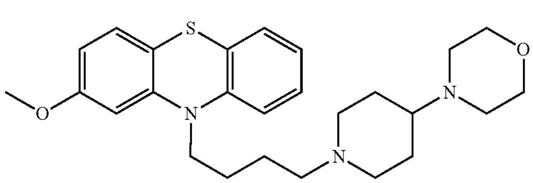 | 1.43-1.52 (m, 2H), 1.55-1.63 (2H), 1.73-1.78 (m, 2H), 1.80-1.87 (m, 4H), 2.11-2.15 (m, 1H), 2.30 (t, J = 7.3 Hz, 2H), 2.51 (t, J = 4.5 Hz, 4H), 2.90 (d, J = 11.5 Hz, 2H), 3.69 (t, J = 4.4 Hz, 4H), 3.75 (s, 3H), 3.83 (t, J = 7.0 Hz, 2H), 6.45-6.46 (m, 2H), 6.84-6.89 (m, 2H), 6.98-7.00 (m, 1H), 7.09-7.12 (m, 2H) |

TABLE 1-continued

| Ex. | Chemical structure | ¹H NMR (ppm) δ |
| --- | --- | --- |
| 63 | 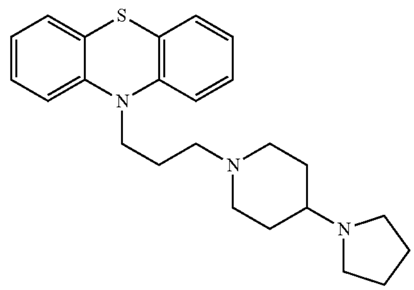 [SMILES: c1ccc2c(c1)Sc1ccccc1N2CCCN1CCC(N2CCCC2)CC1] | 1.46-1.55 (m, 2H), 1.73-1.77 (m, 4H), 1.83 (d, J = 12.8 Hz, 2H), 1.89-1.96 (m, 5H), 2.41 (t, J = 7.0 Hz, 2H), 2.53 (s, 5H), 2.85 (d, J = 11.8 Hz, 2H), 3.90 (t, J = 7.0 Hz, 2H), 6.87-6.90 (m, 4H), 7.10-7.15 (m, 4H) |
| 64 | 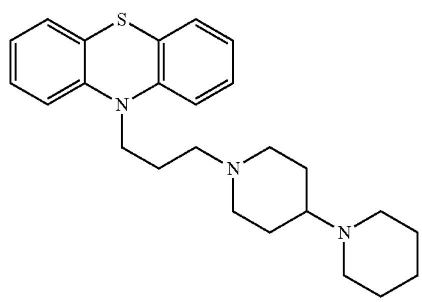 [SMILES: c1ccc2c(c1)Sc1ccccc1N2CCCN1CCC(N2CCCCC2)CC1] | 1.45-1.47 (m, 2H), 1.49-1.56 (m, 2H), 1.58-1.65 (m, 4H), 2.25-2.32 (m, 1H), 2.43 (t, J = 7.2 Hz, 2H), 2.53 (t, J = 7.2 Hz, 2H), 2.93 (d, J = 11.6 Hz, 2H), 3.08 (s, 1H), 3.89 (t, J = 7.0 Hz, 2H), 6.87-6.91 (m, 4H), 7.11-7.15 (m, 4H) |
| 65 | 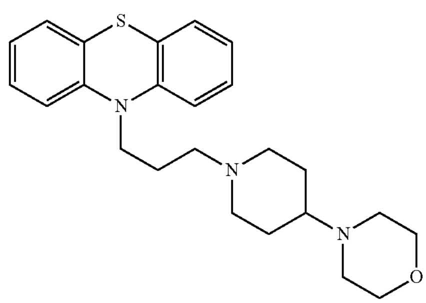 [SMILES: c1ccc2c(c1)Sc1ccccc1N2CCCN1CCC(N2CCOCC2)CC1] | 1.52-1.61 (m, 2H), 1.80 (d, J = 12.5 Hz, 2H), 1.97-2.04 (m, 4H), 2.14-2.21 (m, 1H), 2.50-2.53 (m, 6H), 2.96 (d, J = 11.9 Hz, 2H), 3.70 (t, J = 4.6 Hz, 4H), 3.92 (t, J = 6.8 Hz, 2H), 6.87-6.92 (m, 4H), 7.12-7.16 (m, 4H) |
| 66 | 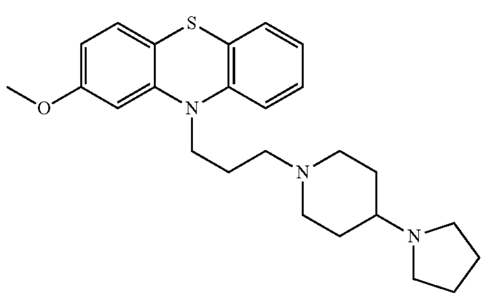 | 1.49-1.58 (m, 2H), 1.78-1.85 (m, 6H), 1.89-1.96 (m, 4H), 1.97-2.26 (m, 1H), 2.42 (t, J = 7.0 Hz, 2H), 2.58 (s, 3H), 186 (d, J = 11.5 Hz, 2H), 3.13 (s, 1H), 3.76 (s, 3H), 3.88 (t, J = 6.9 Hz, 2H), 6.46-6.47 (m, 2H), 6.87-6.90 (m, 2H), 7.00 (d, J = 8.6 Hz, 2H), 7.10-7.14 (m, 2H) |
| 67 | 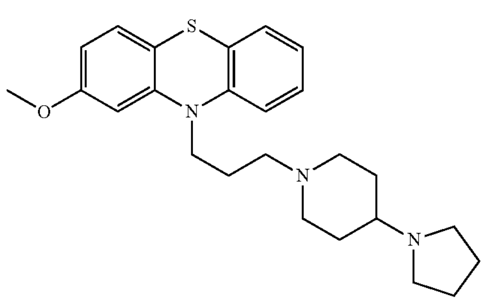 | 1.54-1.63 (m, 2H), 1.81 (d, J = 12.3 Hz, 2H), 1.94-2.04 (m, 4H), 2.15-2.35 (m, 1H), 2.50-2.59 (m, 6H), 2.97 (d, J = 11.9 Hz, 2H), 3.70 (d, J = 4.6 Hz, 4H), 3.77 (s, 3H), 3.92 (t, J = 7.8 Hz, 2H), 6.46-6.49 (m, 2H), 6.87-6.92 (m, 2H), 7.00-7.02 (m, 2H) |

TABLE 1-continued

| Ex. | Chemical structure | $^1$H NMR (ppm) δ |
|---|---|---|
| 68 | 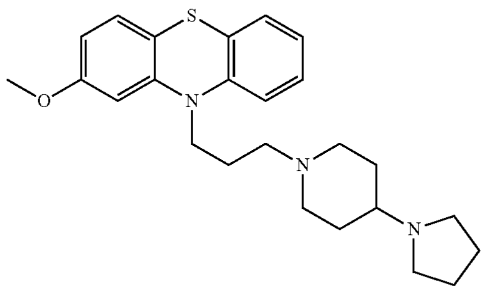 | 1.44-1.46 (m, 2H), 1.49-1.56 (m, 2H), 1.58-1.63 (m, 4H), 1.76 (d, J = 12.2 Hz, 2H), 1.86-2.04 (m, 4H), 2.23-2.31 (m, 1H), 2.42 (t, J = 7.2 Hz, 2H), 2.52 (t, J = 4.9 Hz 4H), 2.92 (d, J = 7.6 Hz, 2H), 2.76 (s, 3H), 3.71 (t, J = 6.9 Hz, 2H), 6.45 (d, J = 2.4 Hz, 1H), 6.47 (s, 1H), 6.87-6.90 (m, 2H), 7.00 (d, J = 8.8 Hz, 1H), 7.10-7.14 (m, 2H) |
| 69 | 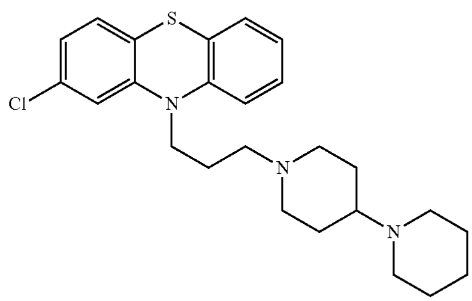 [SMILES: Clc1ccc2c(c1)N(CCCN1CCC(N3CCCCC3)CC1)c1ccccc1S2] | 1.43-1.46 (m, 2H), 1.48-1.55 (m, 2H), 1.57-1.63 (m, 4H), 2.22-2.30 (m, 1H), 2.41 (t, J = 7.2 Hz, 2H), 2.51 (t, J = 4.9 Hz, 4H), 2.92 (d, J = 11.6 Hz, 2H), 3.87 (t, J = 6.9 Hz, 2H), 6.84-6.93 (m, 4H), 6.99 (d, J = 8.1 Hz, 2H), 7.09-7.16 (m, 2H) |
| 70 | 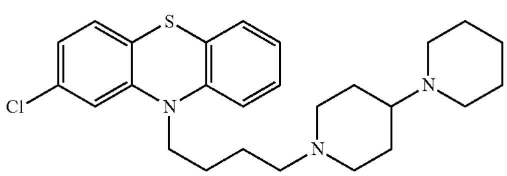 [SMILES: Clc1ccc2c(c1)N(CCCCN1CCC(N3CCCCC3)CC1)c1ccccc1S2] | 1.42-1.46 (m, 2H), 1.50-1.61 (m, 8H), 1.75-1.97 (m, 6H), 2.26-2.27 (m, 1H), 2.31 (t, J = 7.3 Hz, 2H), 2.52 (t, J = 5.0 Hz, 4H), 2.93 (d, J = 11.7 Hz, 2H), 3.83 (t, J = 7.0 Hz, 2H), 6.81 (d, J = 2.0 Hz, 1H), 6.85-6.88 (m, 2H), 6.90-6,93 (m, 1H), 7.00 (d, J = 8.2 Hz, 1H), 7.09-7.16 (m, 2H) |
| 71 | 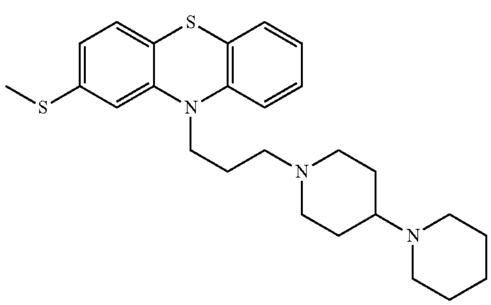 [SMILES: CSc1ccc2c(c1)N(CCCN1CCC(N3CCCCC3)CC1)c1ccccc1S2] | 1.43-1.46 (m, 2H), 1.48-1.55 (m, 2H), 1.58-1.63 (m, 4H), 3.53 (d, J = 121 Hz, 2H) 1.86-1.96 (m, 4H), 2.19-2.30 (m, 1H), 2.42 (t, J = 7.2 Hz, 2H), 2.45 (s, 3H), 3.77 (t, J = 4.9 Hz, 4H), 2.92 (d, J = 11.6 Hz, 2H), 3.89 (t, J = 6.8 Hz, 2H), 6.79 (s, 1H), 6.81 (d, J = 1.6 Hz, 1H), 6.87-6.92 (m, 2H), 7.02 (d, J = 7.0 Hz, 2H), 7.10-7.15 (m, 2H) |
| 72 | 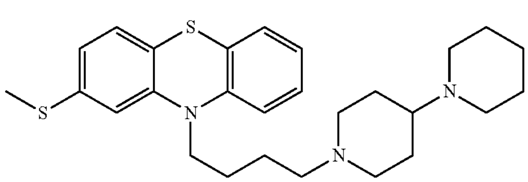 | 1.42-1.44 (m, 2H), 1.49-1.64 (m, 8H), 1.72-1.87 (m, 6H), 2.20-2.32 (m, 6H), 2.46 (s, 3H), 2.49 (t, J = 4.8 Hz, 4H), 2.92 (d, J = 11.5 Hz, 2H), 3.85 (t, J = 6.9 Hz, 2H), 6.77 (d, J = 1.7 Hz, 1H), 6.80-6.82 (m, 1H), 6.87 (d, J = 7.9 Hz, 1H), 6.88-6.92 (m, 1H), 7.03 (d, J = 8.0 Hz, 1H), 7.10-7.15 (m, 2H) |

Example 73

Preparation of 4-(1-(4-(2-fluoro-10H-phenothiazine-10-yl)butyl)piperidin-4-yl)morpholine

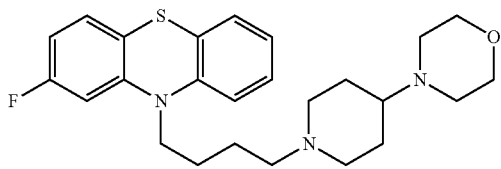 [SMILES: Fc1ccc2c(c1)N(CCCCN1CCC(N3CCOCC3)CC1)c1ccccc1S2]

Step 1:
Preparation of 2-fluoro-10H-phenothiazine

After dissolving CuI (949 mg, 4.99 mmol), calcium carbonate (1.15 g, 83.1 mmol) and L-proline (765 mg, 6.65 mmol) in dimethyl sulfoxide (2 mL) and adding 2-bromo-4-fluoro-1-iodobenzene (2.29 g, 18.3 mmol) and 2-aminothiophenol (5 g, 16.6 mmol) dropwise, the mixture was stirred at 180° C. for 48 hours under reflux. After the reaction was completed, the mixture was extracted with ethyl acetate. The organic layer was dried with magnesium sulfate, filtered under reduced pressure and then concentrated under reduced pressure. The target compound (1.24 mg) was obtained with a yield of 31.13% by separating the residue by chromatography (ethyl acetate/ n-hexane=1/20).

$^1$H NMR (400 MHz, CDCl$_3$): 67 5.82 (1H, s, NH), 6.30 (1H, dd, J=2.52 Hz, CH), 6.52-6.57 (2H, m, 2CH), 6.83 (1H, t, J=7.54 Hz, CH), 6.86-6.91 (1H, m, CH), 6.97-7.02 (2H, m, 2CH).

Step 2:
Preparation of 10-(4-chlorobutyl)-2-fluoro-10H-phenothiazine

After dissolving 2-fluoro-10H-phenothiazine (500 mg, 2.30 mmol) in N,N-dimethylformamide (2 mL), 60% sodium hydride (138 mg 3.45 mmol) and 1-bromo-4-chlorobutane (0.36 mL, 3.11 mmol) were added at 0° C. The reaction mixture was heated at 100° C. for 12 hours under reflux. After the reaction was completed, the mixture was extracted with ethyl acetate and the organic layer was dried with magnesium sulfate, filtered under reduced pressure and then concentrated under reduced pressure. The target compound (500.74 mg) was obtained with a yield of 71.62% by separating the residue by chromatography (ethyl acetate/ n-hexane=1/20).

$^1$H NMR (400 MHz, CDCl$_3$): 67 1.87-2.05 (4H, m, 2CH$_2$), 3.54 (2H, t, J =6.07 Hz, 2CH), 3.88 (2H, t, 6.10 Hz, 2CH), 6.60 (1H, dd, J=2.44 Hz, CH), 6.63-6.67 (1H, m, 1CH), 6.88 (1H, d, 8.08 Hz, 1CH), 6.95 (2H, t, 7.38 Hz, CH), 7.04-7.08 (1H, m, CH), 7.14-7.19 (2H, m, 2CH).

Step 3:
Preparation of 4-(1-(4-(2-fluoro-10H-phenothiazine-10-yl)butyl)piperidin-4-yl)morpholine After dissolving 10-(4-chlorobutyl)-2-fluoro-10H-phenothiazine (100 mg, 0.325 mmol) in 2-butanone (2 mL) and adding potassium carbonate (97.39 mg, 0.65 mmol), sodium iodide (97.4 mg, 0.65 mmol) and 4-morpholinopiperidine (110.6 mg, 0.65 mmol) dropwise, the mixture was heated at 80° C. for 24 hours under reflux. After the reaction was completed, the mixture was extracted with ethyl acetate. The organic layer was dried with magnesium sulfate, filtered under reduced pressure and then concentrated under reduced pressure. The target compound (119.10 mg) was obtained with a yield of 83.00% by separating the residue by chromatography (methanol/ dichloromethane=1/15, 4% ammonia water).

$^1$H NMR (400 MHz, CDCl$_3$): 67 1.45-1.55 (2H, m, CH$_2$), 1.58-1.65 (2H, m, CH$_2$), 1.75-1.90 (6H, m, 3CH$_2$) 2.13-2.20 (1H, m, CH), 2.33 (2H, t, J=7.2 Hz, CH$_2$), 2.53 (4H, t, J=4.6 Hz, 2CH$_2$), 2.93 (2H, d, J=11.6 Hz, CH$_2$), 3.71 (4H, t, J=4.6 Hz, 2CH$_2$), 3.71 (2H, t, J=7.1 Hz, CH$_2$), 6.60-6.64 (1H, m, CH), 6.86-6.88 (1H, m, CH), 6.90-6.94(1H, m, CH), 7.00-7.04 (1H, m, CH), 7.11-7.16 (2H, m, 2CH).

The following phenothiazine compounds were synthesized in the same manner as in Example 72. Their structures and $^1$H NMR data are given in Table 2.

TABLE 2

| 74 | ![structure] | 0.90 (d, J = 6.4 Hz, 3H), 1.17-1.25 (m, 2H), 1.29-1.33 (m, 1H), 1.58 (d, J = 12.8 Hz, 2H), 1.85-1.98 (m, 4H), 2.42 (t, J = 7.2 Hz, 3H), 2.83 (d, J = 11.5 Hz, 2H), 3.85 (t, J = 7.0 Hz, 2H), 6.58-6.64 (m, 2H), 6.88-6.93 (m, 2H), 6.99-7.03 (m, 1H), 7.10-7.15 (m, 2H) |
|---|---|---|
| 75 | ![structure] | 1.45-1.55 (m, 2H), 1.58-1.65 (m, 2H), 1.75-1.90 (m, 6H) 2.13-2.20 (m, 1H), 2.33 (t, J = 7.2 Hz, 2H), 2.53 (t, J = 4.6 Hz, 4H), 2.93 (d, J = 11.6 Hz, 2H), 3.71 (t, J = 4.6 Hz, 4H), 3.83 (t, J = 7.1 Hz, 2H), 6.60-6.64 (m, 2H), 6.86-6.88 (m, 1H), 6.90-6.94 (m, 1H), 7.00-7.04 (m, 1H), 7.11-7.16 (m, 2H) |
| 76 | ![structure] | 0.90 (d, J = 6.3 Hz, 3H), 1.17-1.26 (m, 2H), 1.27-1.37 (m, 1H), 1.57-1.66 (m, 4H), 1.78-1.88 (m, 4H), 2.32 (t, J = 7.4 Hz, 2H), 2.84 (d, J 11.6 Hz, 2H), 3.82 (t, J = 7.2 Hz, 2H), 6.59-6.63 (m, 2H), 6.93 (d, J = .8.4 Hz, 1H) |

| | | |
|---|---|---|
| 77 | (structure) | 1.49-1.65 (m, 4H), 1.79-1.93 (m, 10H), 2.01-2.06 (m, 1H), 2.32 (t, J = 7.3 Hz, 2H), 2.59 (s, 4H), 2.87 (d, J = 11.8 Hz, 2H), 3.83 (t, J = 7.1 Hz, 2H), 6.58-6.64 (m, 2H), 6.87 (d, J = 8.1 Hz, 1H), 6.90-6.94 (m, 1H), 7.00-7.04 (m, 1H), 7.10-7.17 (m, 2H) |
| 78 | (structure) | 1.53-1.63 (m, 9H), 1.76-1.90 (m, 7H), 2.33 (t, J = 7.3 Hz, 3H), 2.54 (s, 4H), 2.95 (d, J = 11.7 Hz, 2H), 3.83 (t, J = 7.1 Hz, 2H), 6.60-6.64 (m, 2H), 6,88 (d, J = 8.1 Hz, 1H), 6.90-6.94 (m, 1H), 7.01-7.05 (m, 1H), 7.11-7.17 (m, 2H) |
| 79 | (structure) | 1.47-1.53 (m, 2H), 1.78 (d, J = 12.3 Hz, 2H), 1.88-1.97 (m, 4H), 2.12-2.18 (m, 1H), 2.43 (t, J = 7.0 Hz, 2H), 2.53 (t, J = 4.6 Hz, 4H), 2.92 (d, J = 11.8 Hz, 2H), 3.71 (t, J = 4.6 Hz, 4H), 3.87 (t, J = 7.0 Hz, 2H), 6.60-6.65 (m, 2H), 6.88-6.94 (m, 2H), 7.00-7.04 (m, 1H), 7.10-7.16 (m, 2H) |
| 80 | (structure) | 1.45-1.48 (m, 2H), 1.52-1.61 (m, 2H), 1.62-1.68 (m, 4H), 1.81 (d, J = 12.0 Hz, 2H), 1.89-1.97 (m, 4H), 2.30-2.37 (m, 1H), 2.42 (t, J = 7.0 Hz, 2H), 2.55-.57 (m, 4H), 2.93 (d, J = 11.2 Hz, 2H), 3.87 (t, J = 6.9 Hz, 2H), 6.59-6.65 (m, 2H), 6.89 (d, J = 8.2 Hz, 1H), 6.92-6.94 (m, 2H), 7.00-7.04 (m, 1H), 7.10-7.17 (m, 2H) |
| 81 | (structure) | 1.47-1.57 (m, 2H), 1.76-1.79 (m, 4H), 1.84 (d, J = 12.6 Hz, 2H), 1.88-2.00 (M, 6H), 2.41 (t, J = 6.7 Hz, 2H), 2.55 (s, 4H), 2.85 (d, J = 11.8 Hz, 1H), 3.87 (t, J = 7.0 Hz, 2H), 6.58-6.63 (m, 2H), 6.88-6.93 (m, 2H), 6.99-7.02 (m, 1H), 7.09-7.15 (m, 2H) |
| 82 | (structure) | 1.49-1.64 (m, 4H), 1.79-1.93 (m, 10H), 2.00-2.07 (m, 1H), 2.23(s, 3H), 2.31 (t, J = 7.4 Hz, 2H), 2.59 (s, 4H), 2.86 (d, J = 11.8 Hz, 2H), 3.83 (t, J = 7.0 Hz, 2H), 6.75 (d, J = 8.1 Hz, 1H), 6.84 (d, J = 8.0 Hz, 2H), 6.87-6.89 (m, 1H), 6.90 (s, 1H), 6,94 (s, 1H), 7.10-7.14 (m, 2H) |
| 83 | (structure) | 1.42-1.45 (m, 2H), 1.53-1.57 (m, 2H), 1.58-1.63 (m, 6H), 1.74-1.88 (m, 6H), 2.223 (s, 3H), 2.30 (t, J = 7.4 Hz, 3H), 2.52 (t, J = 4.8 Hz, 4H), 2.93 (d, J = 11.6 Hz, 2H), 3.83 (t, J = 7.0 Hz, 2H), 6.75 (d, J = 8.0 Hz, 1H), 6.83-6.91 (m, 3H), 6.94 (s, 1H), 7.10-7.13 (m, 2H) |

| | | |
|---|---|---|
| 84 | [3-methylphenothiazine-N-(CH₂)₄-piperidin-4-yl-morpholine structure] | 1.56-1.69 (m, 4H), 1.78-1.86 (m 4H), 1.97 (t, J = 9.8 Hz, 2H), 2.018-2.22 (m, 1H), 2.23 (s, 3H), 2.38 (t, J = 7.4 Hz, 2H), 2.52 (t, J = 4.6 Hz, 4H), 2.96 (d, J = 11.7 Hz, 2H), 3.71 (t, J = 4.6 Hz, 4H), 3.85 (t, J = 6.8 Hz, 3H), 6.75 (d, J = 8.0 Hz, 1H), 6.84-6/93 (m, 3H), 6.95 (s, 1H), 7.11-7.15 (m, 2H) |
| 85 | [3-methylphenothiazine-N-(CH₂)₃-piperidin-4-yl-morpholine structure] | 1.43-1.53 (m, 2H), 1.78 (d, J = 12.4 Hz, 2H), 1.88-1.97 (m, 4H), 2.11-2.17 (m, 1H), 2.23 (s, 3H), 2.43 (t, J = 7.1 Hz, 2H), 2.52 (t, J = 4.6 Hz, 1H), 2.92 (d, J = 11.8 Hz, 2H), 3.71 (t, J = 4.6 Hz, 1H), 3.87 (t, J = 7.0 Hz, 1H), 6.78 (d, J = 8.1 Hz, 1H), 6.85-6.92 (m, 2H), 6.94 (s, 1H), 7.10-7.14 (m, 2H) |
| 86 | [3-methylphenothiazine-N-(CH₂)₃-piperidin-4-yl-piperidine structure] | 1.44-1.46 (m, 2H), 1.50-1.55 (m, 2H), 1.57-1.63 (m, 4H), 1.77 (d, J = 12.2 Hz, 2H), 1.86-1.96 (m, 4H), 2.23 (s, 3H), 2.25-2.29 (m, 1H), 2.42 (t, J = 7.1 Hz, 2H), 2.44-2.52 (m, 4H), 2.93 (d, J = 11.6 Hz, 2H), 3.86 (t, J = 7.0 Hz, 2H), 6.76 (d, J = 8.0 Hz, 1H), 6.85-6.91 (m, 3H), 6.94 (s, 1H), 7.09-7.13 (m, 2H) |
| 87 | [3-methylphenothiazine-N-(CH₂)₃-piperidin-4-yl-pyrrolidine structure] | 1.50-1.60 (m, 2H), 1.80-1.96 (m, 10H), 2.01-2.07 (m, 1H), 2.23 (s, 3H), 2.42 (t, J = 6.9 Hz, 2H), 2.61 (s, 4H), 2.87 (d, J = 11.5 Hz, 2H), 3.88 (t, J = 6.9 Hz, 2H), 6.78 (d, J = 8.0 Hz, 1H), 6.85-6.89 (m, 2H), 6.93 (d, J = 7.8 Hz, 2H), 7.10-7.14 (m, 2H) |
| 88 | [3-cyanophenothiazine-N-(CH₂)₄-piperidin-4-yl-morpholine structure] | 1.44-1.52 (m, 2H), 1.59-1.65 (m, 2H), 1.77-1.90 (m, 6H), 2.13-2.19 (m, 1H0, 2.32 (t, J = 7.1 Hz, 2H), 2.53 (t, J = 4.3 Hz, 4H), 2.92 (d, J = 11.2 Hz, 2H), 3.72 (t, J = 4.6 Hz, 2H), 3.89 (t, J = 7.0 Hz, 2H), 6.85-6.91 (m, 2H), 6.95 (t, J = 7.4 Hz, 2H), 7.10 (d, J = 7.5 Hz, 1H), 7.19 (t, J = 7.3 Hz, 1H), 7.39 (d, J = 1.6 Hz, 1H), 7.39-7.41 (m, 1H) |
| 89 | [3-cyanophenothiazine-N-(CH₂)₄-piperidin-4-yl-pyrrolidine structure] 2HCl | 1.71-1.91 (m, 6H), 1.95-1.99 (m, 3H), 2.08-2.14 (m, 2H), 2.22-2.23 (m, 2H), 2.82-2.86 (m, 2H), 3.02 (s, 4H), 3.48-3.56 (m, 4H), 3.97 (t, J = 6.4 Hz, 2H), 7.04 (t, J = 7.3 Hz, 2H), 7.10 (d, J = 8.4 Hz, 2H), 7.16-7.21 (m,2H), 7.26 (t, J = 8.0 Hz, 1H), 7.60-7.70 (m, 2H), 10.25 (s, 1H), 11.23 (s, 1H) |

TABLE 2-continued

| | | |
|---|---|---|
| 90 | 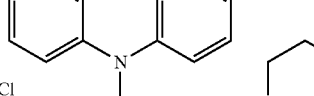 2HCl | 1.39-1.45 (m, 1H) 1.68-1.91 (m, 7H), 2.15-2.31 (m, 4H), 2.90-2.95 (m, 4H), 3.01-3.02 (m, 2H), 3.30-3.33 (m, 2H), 3.38 (s, 4H), 3.55 (d, J = 11.9 Hz, 2H), 3.96 (t, J = 6.5 Hz, 2H), 7.00-7.08 (m, 1H), 7.12 (d, J = 8.3 Hz, 1H), 7.18 (t, J = 8.6 Hz, 2H), 7.25 (t, J = 7.8 Hz, 1H), 7.59-7.69 (m, 2H), 10.76 (s, 1H), 10.97 (s, 1H) |
| 91 | 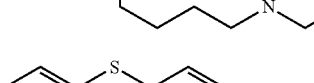 | 1.49-1.53 (m, 2H), 1.58-1.62 (m, 2H), 1.76-1.79 (m, 3H), 1.81-1.85 (m, 4H), 1.88-1.91(m, 2H), 1.94-1.98 (m, 1H), 2.23 (s, 3H), 2.31 (t, J = 7.4 Hz, 1H), 2.55 (s, 4H), 2.86 (d, J = 11.8 Hz, 2H), 3.83 (t, J = 7.1 Hz, 2H), 6.75 (d, J = 8.0 Hz, 1H), 6.83-6.92 (m, 2H), 6.94 (s, 1H), 7.10-7.14 (m, 2H) |
| 92 | 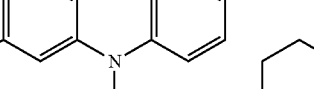 | 1.43-1.45 (m, 2H), 1.53-1.56 (m, 2H), 1.57-1.62 (m, 6H), 1.75-1.88 (m, 7H), 2.23 (s, 3H), 2.31 (t, J = 7.4 Hz, 2H), 2.52-2.54 (m, 4H), 2.93 (d, J = 11.5 Hz, 2H), 3.83 (t, J = 7.0 Hz, 2H), 6.75 (d, J = 8.0 Hz, 1H), 6.83-6.92 (m, 3H), 6.94 (s, 1H), 7.10-7.14 (m, 2H) |

The novel compound represented by Chemical Formula 1 according to the present invention may be prepared into various formulations depending on purposes. The followings are some formulation examples containing the compound represented by Chemical Formula 1 according to the present invention as an active ingredient. However, the present invention is not limited thereto.

Formulation Examples

Formulation Example 1: Tablet (Direct Compression)

A tablet was prepared by sieving the active ingredient (5.0 mg), mixing with lactose (14.1 mg), crospovidone USNF (0.8 mg) and magnesium stearate (0.1 mg) and compressing the mixture.

Formulation Example 2: Tablet (Wet Granulation)

The active ingredient (5.0 mg) was sieved and mixed with lactose (16.0 mg) and starch (4.0 mg). The mixture was prepared into fine granules by adding an adequate amount of a solution of polysorbate 80 (0.3 mg) dissolved in pure water. After drying and sieving, the fine granules were mixed with colloidal silicon dioxide (2.7 mg) and magnesium stearate (2.0 mg). A tablet was prepared by compressing the fine granules.

Formulation Example 3: Powder and Capsule

The active ingredient (5.0 mg) was sieved and mixed with lactose (14.8 mg), polyvinylpyrrolidone (10.0 mg) and magnesium stearate (0.2 mg). The mixture was filled in a hard No. 5 gelatin capsule using an appropriate apparatus.

Formulation Example 4: Injection

An injection was prepared with the active ingredient (100 mg), mannitol (180 mg), $Na_2HPO_4 \cdot 12H_2O$ (26 mg) and distilled water (2974 mg).

The physiological activity of the compound represented by Chemical Formula 1 according to the present invention was evaluated in Experimental Examples as described below.

Experimental Example

Evaluation of Physiological Activity

Calcium Imaging ($Ca^{2+}$ Imaging)

Calcium imaging was conducted as follows in order to measure the change in the calcium level in lung cancer cells (glioblastoma cells) by TFP (trifluoperazine) and the phenothiazine derivative represented by Chemical Formula 1 according to the present invention. First, after placing a polylysine (PDL)-coated coverslip on a 24-well plate, $2 \times 10^4$ U87MG cells detached by treating with trypsin were seeded thereupon. On the next day, the coverslip was incubated at room temperature for 1 hour in a Fura-2 solution (5 µM Fura-2 AM, 1 µM pluronic acid in HEPES buffer, pH 7.4) and washed twice with a HEPES buffer (10 mM HEPES, 150 mM NaCl, 3 mM KCl, 2 mM $CaCl_2$, 1 mM $MgCl_2$, 22 mM sucrose, 10 mM glucose, pH 7.4). The washed coverslip was mounted in a bath adapter (bath adapter) and placed under a calcium imaging microscope (Olympus IX71). After connecting a bath line to the bath adapter, the change in the calcium level of the cells was recorded for 300 seconds (4-second intervals; 340 nm, 380 nm, 340/380 nm ratio) by running a calcium imaging program (Imaging Workbench 6.0, Indec Inc.). After flowing a HEPES buffer for 50 seconds for setting of the baseline, a TFP (trifluoperazine) solution or solution of the phenothiazine derivative represented by Chemical Formula 1 (100 µM in HEPES buffer) were flown as test solutions for 100 seconds and then a HEPES buffer was flown again for 150 seconds. All the test solutions were prepared by diluting a 50 mM stock solution to 100 µM with a HEPES buffer. For analysis of the change of intracellular calcium level by the phenothiazine derivative represented by Chemical Formula 1, data files were read using a calcium imaging analysis program (Clampfit 9.2, Axon Inc.) and only the 340/380 ratio values were taken. The values recorded for the first 50 seconds were set to "0" and graphs were rearranged. Then, the average reactivity to the phenothiazine derivative represented by Chemical Formula 1 for 200 seconds was calculated relative to the average reactivity to TFP (trifluoperazine) for 200 seconds as 100%.

FIG. 1 shows the calcium imaging experiment result for the phenothiazine derivative represented by Chemical Formula 1.

Figure 2:
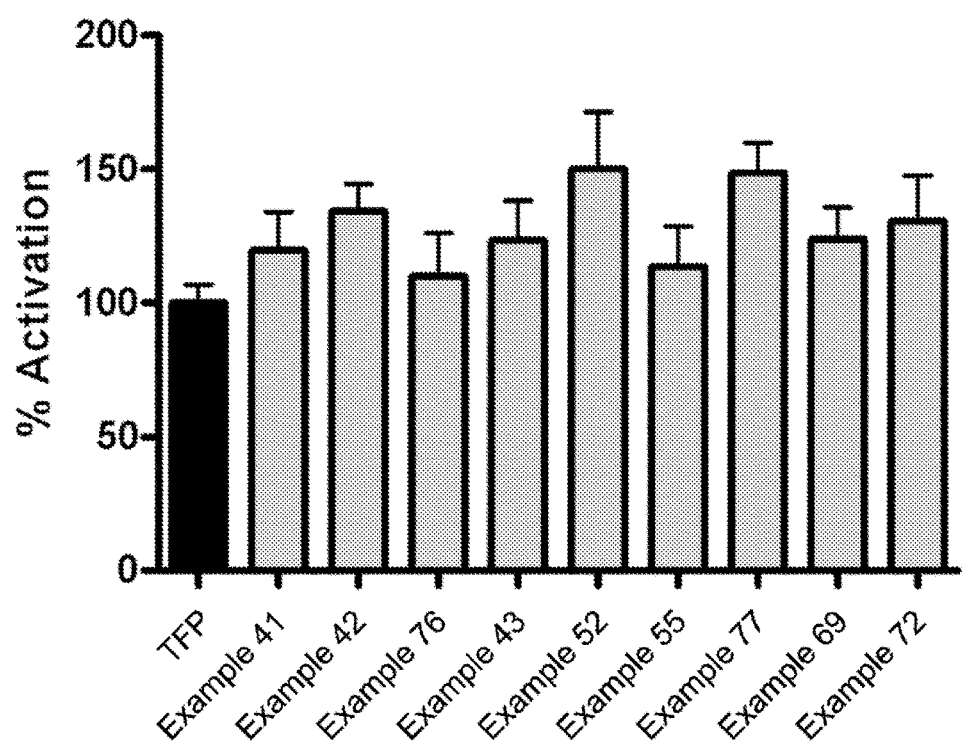
FIG. 2 shows compounds that show superior reactivity in a calcium imaging experiment result as compared to TFP (trifluoperazine).

In FIG. 2 and Table 3, the compounds that showed superior reactivity in the calcium imaging experiment as compared to TFP (trifluoperazine) are shown.

TABLE 3

| Test compounds | Reactivity (%) |
|---|---|
| TFP | 100 |
| Example 41 | 120 |
| Example 42 | 134 |
| Example 76 | 110 |
| Example 43 | 123 |
| Example 52 | 150 |
| Example 55 | 114 |
| Example 77 | 149 |
| Example 69 | 124 |
| Example 72 | 131 |

What is claimed is:

1. A compound selected from a phenothiazine derivative represented by Chemical Formula 1 and pharmaceutically acceptable salt thereof:

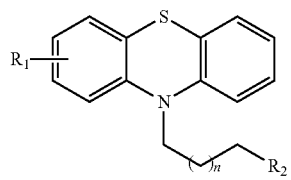

[Chemical Formula 1]

wherein
$R_1$ is a hydrogen atom, a $C_1$-$C_{10}$ alkyl group, a $C_1$-$C_{10}$ haloalkyl group or a $C_1$-$C_{10}$ alkylthio group;
$R_2$ is

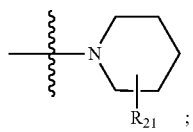

$R_{21}$ is a 5- to 7-membered heterocycle group containing one to three hetero atom(s) selected from nitrogen and oxygen atom(s), wherein the heterocycle group may be substituted or unsubstituted with one to three substituent(s) selected from a group consisting of halo, nitro, $C_1$-$C_6$ alkyl and $C_1$-$C_6$ alkoxy; and
n is an integer 1 or 2.

2. The compound according to claim 1, wherein
the $R_1$ is a hydrogen atom, a methyl group, a trifluoromethyl group or a methylthio group;
the $R_2$ is

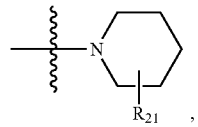

wherein $R_{21}$ is a morpholino group or a pyrrolidinyl group; and
the n is an integer 1 or 2.

3. The compound according to claim 1, wherein
the $R_1$ is a hydrogen atom, a methyl group, a trifluoromethyl group or a methylthio group;
the $R_2$ is 4,4-difluoropiperidin-1-yl group, a 4-(hydroxyethyl)piperidin-1-yl group, a 4-phenylpiperidin-1-yl group, a 4-(pyrrolidin-1-yl)piperidin-1-yl group, a 1,4'-bipiperidin-1-yl group or a 4-morpholinopiperidin-1-yl group; and
the n is an integer 1 or 2.

4. The compound according to claim 1, which is selected from a group consisting of:
compound 41. 4-(1-(4-(2-(trifluoromethyl)-10H-phenothiazine;-10-yl)butyl)piperidin-4-yl) morpholine;
compound 42. 10-(4-(4-(pyrrolidin-1-yl)piperidin-1-yl)butyl)-2-(trifluoromethyl)10H- phenothiazine;
compound 43. 10-(4-(1,4'-bipiperidin-1'-yl)butyl)-2-(trifluoromethyl)-10H-phenothiazine;
compound 45. 4-(1-(4-(2-(methylthio)-10H-phenothiazine;-10-yl)butyl)piperidin-4-yl) morpholine;
compound 46. 4-(1-(3-(2-(trifluoromethyl)-10H-phenothiazine;-10-yl)propyl)piperidin-4-yl) morpholine;
compound 48. 10-(3-(4-(pyrrolidin-1-yl)piperidin-1-yl)propyl)-2-(trifluoromethyl)-10H-phenothiazine;
compound 52. 2-(methylthio)-10-(4-(4-(pyrrolidin-1-yl)piperidin-1-yl)butyl)-10H-phenothiazine;
compound 53. 10-(3-(1,4'-bipiperidin-1'-yl)propyl)-2-(trifluoromethyl)-10H-phenothiazine;
compound 54. 4-(1-(3-(2-(methylthio)-10H-phenothiazine;-10-yl)propyl)piperidin-4-yl) morpholine;
compound 55. 2-(methylthio)-10-(3-(4-(pyrrolidin-1-yl)piperidin-1-yl)propyl)-10H-phenothiazine;
compound 57. 4-(1-(4-(10H-phenothiazine;-10-yl)butyl)piperidin-4-yl)morpholine;
compound 58. 10-(4-(4-(pyrrolidin-1-yl)piperidin-1-yl)butyl)-10H-phenothiazine;
compound 59. 10-(4-(1,4'-bipiperidin-1'-yl)butyl)-10H-phenothiazine;
compound 63. 10-(3-(4-(pyrrolidin-1-yl)piperidin-1-yl)propyl)-10H-phenothiazine;
compound 64. 10-(3-(1,4'-bipiperidin-1'-yl)propyl)-10H-phenothiazine;
compound 65. 4-(1-(3-(10H-phenothiazine;-10-yl)propyl)piperidin-4-yl)morpholine;
compound 71. 10-(3-(1,4'-bipiperidin-1'-yl)propyl)-2-(methylthio)-10H-phenothiazine;
compound 72. 10-(4-(1,4'-bipiperidin-1'-yl)butyl)-2-(methylthio)-10H-phenothiazine;
compound 82. 3-methyl-10-(4-(4-(pyrrolidin-1-yl)piperidin-1-yl)butyl)-10H-phenothiazine;
compound 83. 10-(4-(1,4'-bipiperidin-1'-yl)butyl)-3-methyl-10H-phenothiazine;
compound 84. 4-(1-(4-(3-methyl-10H-phenothiazine;-10-yl)butyl)piperidin-4-yl) morpholine;

49 compound 85. 4-(1-(3-(3-methyl-10H-phenothiazine;-10-yl)propyl)piperidin-4-yl) morpholine;
compound 86. 10-(3-(1,4'-bipiperidin-1'-yl)propyl)-3-methyl-10H-phenothiazine;
compound 87. 3-methyl-10-(3-(4-(pyrrolidin-1-yl)piperidin-1-yl)propyl)-10H-phenothiazine;
compound 91. 2-methyl-10-(4-(4-(pyrrolidin-1-yl)piperidin-1-yl)butyl)-10H-phenothiazine; and
compound 92. 10-(4-(1,4'-bipiperidin-1'-yl)butyl)-2-methyl-10H-phenothiazine.

5. A pharmaceutical composition comprising one or more compound(s) selected from a phenothiazine derivative represented by Formula 1 according to claim 1 and a pharmaceutically acceptable salt thereof as an active ingredient.

6. A method for preparing a compound selected from a phenothiazine derivative represented by Chemical Formula 1 and pharmaceutically acceptable salt thereof:

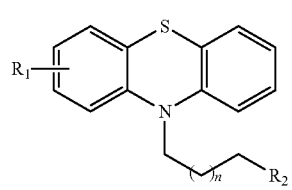

[Chemical Formula 1]

wherein
$R_1$ is a hydrogen atom, a halogen atom, a carbonitrile group, a $C_1$-$C_{10}$ alkyl group, a $C_1$-$C_{10}$ haloalkyl group, a $C_1$-$C_{10}$ alkoxy group or a $C_1$-$C_{10}$ alkylthio group;
$R_2$ is

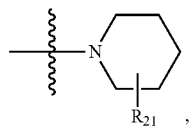

$R_{21}$ is one to three halogen atom(s), a $C_1$-$C_6$ hydroxyalkyl group, a $C_6$-$C_{10}$ aryl group, a $C_6$-$C_{10}$ aryl-$C_1$-$C_6$ alkyl group or a 5- to 7-membered heterocycle group containing one to three hetero atom(s) selected from nitrogen and oxygen atom(s), wherein the aryl or heterocycle group may be substituted or unsubstituted with one to three substituent(s) selected from a group consisting of halo, nitro, $C_1$-$C_6$ alkyl and $C_1$-$C_6$ alkoxy; and

50 n is an integer 1 or 2, the method comprising,
reacting a phenothiazine represented by Chemical Formula (2) with a dihaloalkane represented by Chemical Formula (3) to thereby prepare a haloalkyl-substituted phenothiazine compound represented by Chemical Formula (4), and
reacting the haloalkyl-substituted phenothiazine compound represented by Chemical Formula (4) with an amine compound represented by $R_2$—H to thereby prepare the phenothiazine derivative represented by Chemical Formula (1):

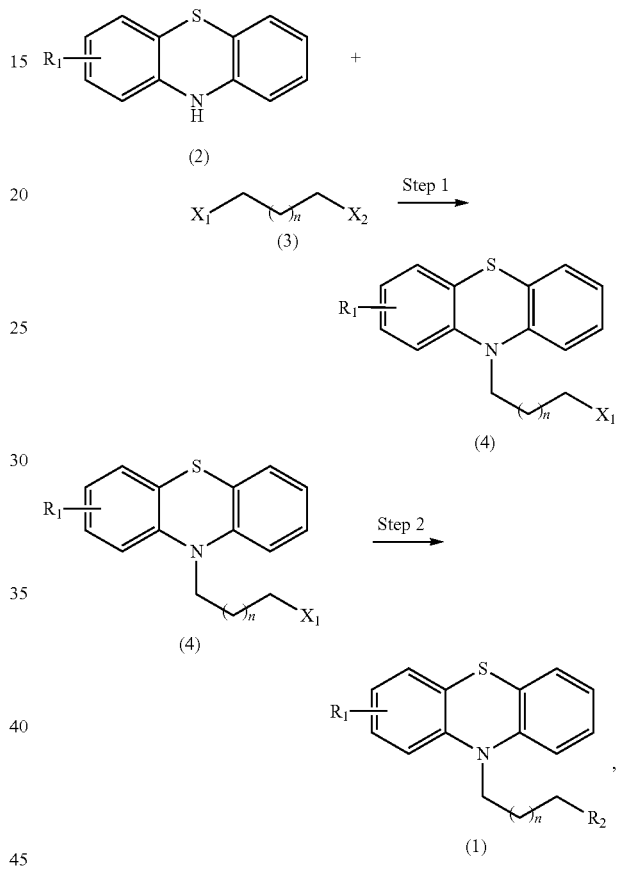

wherein each of $R_1$, $R_2$, and n is the same as defined above in Chemical Formula 1 and each of $X_1$ and $X_2$, which are identical or different, is a halogen atom.

* * * * *